US010287462B2

(12) United States Patent
Hampson et al.

(10) Patent No.: US 10,287,462 B2
(45) Date of Patent: May 14, 2019

(54) BINDERS AND ASSOCIATED PRODUCTS

(71) Applicants: KNAUF INSULATION SPRL, Vise (BE); KNAUF INSULATION, INC., Shelbyville, IN (US)

(72) Inventors: Carl Hampson, St. Helens (GB); Benedicte Pacorel, Auckland (NZ); Roger Jackson, St. Helens (GB)

(73) Assignees: Knauf Insulation, Inc., Shelbyville, IN (US); Knauf Insulation SPRL, Vise (BE)

( * ) Notice: Subject to any disclaimer, the term of this patent is extended or adjusted under 35 U.S.C. 154(b) by 0 days.

(21) Appl. No.: 15/702,087

(22) Filed: Sep. 12, 2017

(65) Prior Publication Data
US 2018/0002577 A1   Jan. 4, 2018

Related U.S. Application Data

(63) Continuation of application No. 15/172,432, filed on Jun. 3, 2016, now abandoned, which is a continuation of application No. 14/390,445, filed as application No. PCT/EP2013/057151 on Apr. 4, 2013, now abandoned.

(30) Foreign Application Priority Data

Apr. 5, 2012 (GB) .................................. 1206193.3

(51) Int. Cl.
| C09J 161/20 | (2006.01) |
| C09J 161/22 | (2006.01) |
| B27N 3/00 | (2006.01) |
| C07H 5/04 | (2006.01) |
| B29C 71/00 | (2006.01) |
| B29K 79/00 | (2006.01) |
| F16L 59/02 | (2006.01) |
| C09J 105/00 | (2006.01) |

(52) U.S. Cl.
CPC ............ *C09J 105/00* (2013.01); *B29C 71/00* (2013.01); *C07H 5/04* (2013.01); *C09J 161/20* (2013.01); *C09J 161/22* (2013.01); *F16L 59/028* (2013.01); *B27N 3/002* (2013.01); *B29K 2079/00* (2013.01); *B29K 2405/00* (2013.01)

(58) Field of Classification Search
CPC .... C09J 161/20; C09J 161/161; C09J 161/22; C09J 105/00
See application file for complete search history.

(56) References Cited

U.S. PATENT DOCUMENTS

| 1,801,052 A | 4/1931 | Meigs |
| 1,801,053 A | 4/1931 | Meigs |
| 1,886,353 A | 11/1932 | Novotny |
| 1,902,948 A | 3/1933 | Castle |
| 1,964,263 A | 6/1934 | Krenke |
| 2,198,874 A | 4/1940 | Leighton |
| 2,215,825 A | 9/1940 | Wallace |
| 2,261,295 A | 11/1941 | Schlack |
| 2,362,086 A | 11/1944 | Eastes |
| 2,371,990 A | 3/1945 | Hanford |
| 2,392,105 A | 1/1946 | Sussman |
| 2,442,989 A | 6/1948 | Sussman |
| 2,500,665 A | 3/1950 | Courtright |
| 2,518,956 A | 8/1950 | Sussman |
| 2,875,073 A | 2/1959 | Gogek |
| 2,894,920 A | 7/1959 | Ramos |
| 2,965,504 A | 12/1960 | Gogek |
| 3,038,462 A | 6/1962 | Bohdan |
| 3,138,473 A | 6/1964 | Floyd |
| 3,222,243 A | 12/1965 | Gaston |
| 3,231,349 A | 1/1966 | Stalego |
| 3,232,821 A | 2/1966 | Banks |
| 3,297,419 A | 1/1967 | Eyre, Jr. |
| 3,513,001 A | 5/1970 | Woodhead |
| 3,551,365 A | 12/1970 | Matalon |
| 3,784,408 A | 1/1974 | Jaffe |
| 3,791,807 A | 2/1974 | Etzel |
| 3,802,897 A | 4/1974 | Bovier |
| 3,809,664 A | 5/1974 | Burr |
| 3,826,767 A | 7/1974 | Hoover |
| 3,856,606 A | 12/1974 | Fan |
| 3,867,119 A | 2/1975 | Takeo |

(Continued)

FOREIGN PATENT DOCUMENTS

| AU | 8538765 | 8/1985 |
| AU | 9640921 | 7/1997 |

(Continued)

OTHER PUBLICATIONS

International Search Report and Written Opinion received for PCT Application No. PCT/EP2013/057151, dated Sep. 25, 2013, 10 pages.
International Preliminary Report on Patentability received for PCT Application No. PCT/EP2013/057151, dated Aug. 7, 2014, 9 pages.
Demand for PCT Chapter II received for PCT Application No. PCT/EP2013/057151, mailed on Feb. 5, 2014, 23 pages.
Written Opinion of the International Preliminary Examination Authority (WOIPEA) for PCT Application No. PCT/EP2013/057151, dated May 7, 2014, 5 pages.

(Continued)

*Primary Examiner* — Liam J Heincer
(74) *Attorney, Agent, or Firm* — Knauf Insulation, Inc.; James K. Blodgett; Brandon N. Hudder

(57) ABSTRACT

The present invention relates to a water-soluble pre-reacted binder composition, a method of its manufacture, a use of said pre-reacted binder composition, a method of manufacturing a collection of matter bound by a polymeric binder, a binder solution or dispersion comprising said pre-reacted binder composition, as well as products comprising the pre-reacted binder composition in a cured state.

24 Claims, 18 Drawing Sheets

(56) References Cited

U.S. PATENT DOCUMENTS

| | | |
|---|---|---|
| 3,907,724 A | 9/1975 | Higginbottom |
| 3,911,048 A | 10/1975 | Nistri |
| 3,919,134 A | 11/1975 | Higginbottom |
| 3,922,466 A | 11/1975 | Bell |
| 3,955,031 A | 5/1976 | Jones |
| 3,956,204 A | 5/1976 | Higginbottom |
| 3,961,081 A | 6/1976 | McKenzie |
| 3,971,807 A | 7/1976 | Brack |
| 4,014,726 A | 3/1977 | Fargo |
| 4,028,290 A | 6/1977 | Reid |
| 4,048,127 A | 9/1977 | Gibbons |
| 4,054,713 A | 10/1977 | Sakaguchi |
| 4,085,076 A | 4/1978 | Gibbons |
| 4,097,427 A | 6/1978 | Aitken |
| 4,107,379 A | 8/1978 | Stofko |
| 4,109,057 A | 8/1978 | Nakamura |
| 4,144,027 A | 3/1979 | Habib |
| 4,148,765 A | 4/1979 | Nelson |
| 4,183,997 A | 1/1980 | Stofko |
| 4,184,986 A | 1/1980 | Krasnobajew |
| 4,186,053 A | 1/1980 | Krasnobajew |
| 4,201,247 A | 5/1980 | Shannon |
| 4,201,857 A | 5/1980 | Krasnobajew |
| 4,217,414 A | 8/1980 | Walon |
| 4,233,432 A | 11/1980 | Curtis, Jr. |
| 4,246,367 A | 1/1981 | Curtis, Jr. |
| 4,259,190 A | 3/1981 | Fahey |
| 4,265,963 A | 5/1981 | Matalon |
| 4,278,573 A | 7/1981 | Tessler |
| 4,296,173 A | 10/1981 | Fahey |
| 4,301,310 A | 11/1981 | Wagner |
| 4,310,585 A | 1/1982 | Shannon |
| 4,322,523 A | 3/1982 | Wagner |
| 4,330,443 A | 5/1982 | Rankin |
| 4,333,484 A | 6/1982 | Keritsis |
| 4,357,194 A | 11/1982 | Stofko |
| 4,361,588 A | 11/1982 | Herz |
| 4,379,101 A | 4/1983 | Smith |
| 4,393,019 A | 7/1983 | Geimer |
| 4,396,430 A | 8/1983 | Matalon |
| 4,400,496 A | 8/1983 | Butler |
| 4,464,523 A | 8/1984 | Neigel |
| 4,506,684 A | 3/1985 | Keritsis |
| 4,520,143 A | 5/1985 | Jellinek |
| 4,524,164 A | 6/1985 | Viswanathan |
| 4,631,226 A | 12/1986 | Jellinek |
| 4,654,259 A | 3/1987 | Stofko |
| 4,668,716 A | 5/1987 | Pepe |
| 4,692,478 A | 9/1987 | Viswanathan |
| 4,714,727 A | 12/1987 | Hume, III |
| 4,720,295 A | 1/1988 | Bronshtein |
| 4,754,056 A | 6/1988 | Ansel |
| 4,761,184 A | 8/1988 | Markessini |
| 4,780,339 A | 10/1988 | Lacourse |
| 4,828,643 A | 5/1989 | Newman |
| 4,845,162 A | 7/1989 | Schmitt |
| 4,906,237 A | 3/1990 | Johansson |
| 4,912,147 A | 3/1990 | Pfoehler |
| 4,918,861 A | 4/1990 | Carpenter |
| 4,923,980 A | 5/1990 | Blomberg |
| 4,950,444 A | 8/1990 | Deboufie |
| 4,988,780 A | 1/1991 | Das |
| 4,992,519 A | 2/1991 | Mukherjee |
| 5,001,202 A | 3/1991 | Denis |
| 5,013,405 A | 5/1991 | Izard |
| 5,037,930 A | 8/1991 | Shih |
| 5,041,595 A | 8/1991 | Yang |
| 5,089,342 A | 2/1992 | Dhein |
| 5,095,054 A | 3/1992 | Lay |
| 5,106,615 A | 4/1992 | Dikstein |
| 5,114,004 A | 5/1992 | Isono |
| 5,123,949 A | 6/1992 | Thiessen |
| 5,124,369 A | 6/1992 | Vandichel |
| 5,128,407 A | 7/1992 | Layton |
| 5,143,582 A | 9/1992 | Arkens |
| 5,151,465 A | 9/1992 | Le-Khac |
| 5,167,738 A | 12/1992 | Bichot |
| 5,198,492 A | 3/1993 | Stack |
| 5,217,741 A | 6/1993 | Kawachi |
| 5,218,048 A | 6/1993 | Abe |
| 5,240,498 A | 8/1993 | Matalon |
| 5,278,222 A | 1/1994 | Stack |
| 5,300,144 A | 4/1994 | Adams |
| 5,300,192 A | 4/1994 | Hansen |
| 5,308,896 A | 5/1994 | Hansen |
| 5,318,990 A | 6/1994 | Strauss |
| 5,336,753 A | 8/1994 | Jung |
| 5,336,755 A | 8/1994 | Pape |
| 5,336,766 A | 8/1994 | Koga |
| 5,340,868 A | 8/1994 | Strauss |
| 5,352,480 A | 10/1994 | Hansen |
| 5,371,194 A | 12/1994 | Ferretti |
| 5,387,665 A | 2/1995 | Misawa |
| 5,389,716 A | 2/1995 | Graves |
| 5,393,849 A | 2/1995 | Srinivasan |
| 5,416,139 A | 5/1995 | Zeiszler |
| 5,421,838 A | 6/1995 | Gosset |
| 5,424,418 A | 6/1995 | Duflot |
| 5,434,233 A | 7/1995 | Kiely |
| 5,447,977 A | 9/1995 | Hansen |
| 5,470,843 A | 11/1995 | Stahl |
| 5,480,973 A | 1/1996 | Goodlad |
| 5,492,756 A | 2/1996 | Seale |
| 5,498,662 A | 3/1996 | Tanaka |
| 5,503,920 A | 4/1996 | Alkire |
| 5,534,612 A | 7/1996 | Taylor |
| 5,536,766 A | 7/1996 | Seyffer |
| 5,538,783 A | 7/1996 | Hansen |
| 5,543,215 A | 8/1996 | Hansen |
| 5,545,279 A | 8/1996 | Hall |
| 5,547,541 A | 8/1996 | Hansen |
| 5,547,745 A | 8/1996 | Hansen |
| 5,550,189 A | 8/1996 | Qin |
| 5,554,730 A | 9/1996 | Woiszwillo |
| 5,562,740 A | 10/1996 | Cook |
| 5,571,618 A | 11/1996 | Hansen |
| 5,578,678 A | 11/1996 | Hartmann |
| 5,580,856 A | 12/1996 | Prestrelski |
| 5,582,682 A | 12/1996 | Ferretti |
| 5,583,193 A | 12/1996 | Aravindakshan |
| 5,589,256 A | 12/1996 | Hansen |
| 5,589,536 A | 12/1996 | Golino |
| 5,607,759 A | 3/1997 | Hansen |
| 5,608,011 A | 3/1997 | Eck |
| 5,609,727 A | 3/1997 | Hansen |
| 5,614,570 A | 3/1997 | Hansen |
| 5,620,940 A | 4/1997 | Birbara |
| 5,621,026 A | 4/1997 | Tanaka |
| 5,633,298 A | 5/1997 | Arfaei |
| 5,641,561 A | 6/1997 | Hansen |
| 5,643,978 A | 7/1997 | Darwin |
| 5,645,756 A | 7/1997 | Dubin |
| 5,660,904 A | 8/1997 | Andersen |
| 5,661,213 A | 8/1997 | Arkens |
| 5,670,585 A | 9/1997 | Taylor |
| 5,672,418 A | 9/1997 | Hansen |
| 5,672,659 A | 9/1997 | Shalaby |
| 5,690,715 A | 11/1997 | Schiwek |
| 5,691,060 A | 11/1997 | Levy |
| 5,693,411 A | 12/1997 | Hansen |
| 5,719,092 A | 2/1998 | Arrington |
| 5,719,228 A | 2/1998 | Taylor |
| 5,756,580 A | 5/1998 | Natori |
| 5,763,524 A | 6/1998 | Arkens |
| 5,788,243 A | 8/1998 | Harshaw |
| 5,788,423 A | 8/1998 | Perkins |
| 5,807,364 A | 9/1998 | Hansen |
| 5,855,987 A | 1/1999 | Margel |
| 5,863,985 A | 1/1999 | Shalaby |
| 5,885,337 A | 3/1999 | Nohr |
| 5,895,804 A | 4/1999 | Lee |
| 5,905,115 A | 5/1999 | Luitjes |
| 5,916,503 A | 6/1999 | Rettenbacher |
| 5,919,528 A | 7/1999 | Huijs |

(56) References Cited

U.S. PATENT DOCUMENTS

| | | | |
|---|---|---|---|
| 5,919,831 | A | 7/1999 | Philipp |
| 5,922,403 | A | 7/1999 | Tecle |
| 5,925,722 | A | 7/1999 | Exner |
| 5,929,184 | A | 7/1999 | Holmes-Farley |
| 5,929,196 | A | 7/1999 | Kissel |
| 5,932,344 | A | 8/1999 | Ikemoto |
| 5,932,665 | A | 8/1999 | DePorter |
| 5,932,689 | A | 8/1999 | Arkens |
| 5,942,123 | A | 8/1999 | McArdle |
| 5,954,869 | A | 9/1999 | Elfersy |
| 5,977,224 | A | 11/1999 | Cheung |
| 5,977,232 | A | 11/1999 | Arkens |
| 5,981,719 | A | 11/1999 | Woiszwillo |
| 5,983,586 | A | 11/1999 | Berdan, II |
| 5,990,216 | A | 11/1999 | Cai |
| 5,993,709 | A | 11/1999 | Bonomo |
| 6,022,615 | A | 2/2000 | Rettenbacher |
| 6,067,821 | A | 5/2000 | Jackson |
| 6,071,549 | A | 6/2000 | Hansen |
| 6,071,994 | A | 6/2000 | Hummerich |
| 6,072,086 | A | 6/2000 | James |
| 6,077,883 | A | 6/2000 | Taylor |
| 6,090,925 | A | 7/2000 | Woiszwillo |
| 6,114,033 | A | 9/2000 | Ikemoto |
| 6,114,464 | A | 9/2000 | Reck |
| 6,133,347 | A | 10/2000 | Vickers, Jr. |
| 6,136,916 | A | 10/2000 | Arkens |
| 6,139,619 | A | 10/2000 | Zaretskiy |
| 6,143,243 | A | 11/2000 | Gershun |
| 6,171,444 | B1 | 1/2001 | Nigam |
| 6,171,654 | B1 | 1/2001 | Salsman |
| 6,180,037 | B1 | 1/2001 | Andersen |
| 6,194,512 | B1 | 2/2001 | Chen |
| 6,210,472 | B1 | 4/2001 | Kwan |
| 6,221,958 | B1 | 4/2001 | Shalaby |
| 6,221,973 | B1 | 4/2001 | Arkens |
| 6,231,721 | B1 | 5/2001 | Quick |
| 6,274,661 | B1 | 8/2001 | Chen |
| 6,281,298 | B1 | 8/2001 | Papsin, Jr. |
| 6,299,677 | B1 | 10/2001 | Johnson |
| 6,299,936 | B1 | 10/2001 | Reck |
| 6,307,732 | B1 | 10/2001 | Tsubaki |
| 6,310,227 | B1 | 10/2001 | Sarama |
| 6,313,102 | B1 | 11/2001 | Colaco |
| 6,319,683 | B1 | 11/2001 | James |
| 6,331,350 | B1 | 12/2001 | Taylor |
| 6,331,513 | B1 | 12/2001 | Zaid |
| 6,340,411 | B1 | 1/2002 | Hansen |
| 6,348,530 | B1 | 2/2002 | Reck |
| 6,365,079 | B1 | 4/2002 | Winkler |
| 6,372,077 | B1 | 4/2002 | Tecle |
| 6,379,739 | B1 | 4/2002 | Formanek |
| 6,395,856 | B1 | 5/2002 | Petty |
| 6,403,665 | B1 | 6/2002 | Sieker |
| 6,407,225 | B1 | 6/2002 | Mang |
| 6,410,036 | B1 | 6/2002 | De Rosa |
| 6,440,204 | B1 | 8/2002 | Rogols |
| 6,461,553 | B1 | 10/2002 | Hansen |
| 6,468,442 | B2 | 10/2002 | Bytnar |
| 6,468,730 | B2 | 10/2002 | Fujiwara |
| 6,469,120 | B1 | 10/2002 | Elfersy |
| 6,475,552 | B1 | 11/2002 | Shah |
| 6,482,875 | B2 | 11/2002 | Lorenz |
| 6,495,656 | B1 | 12/2002 | Haile |
| 6,521,339 | B1 | 2/2003 | Hansen |
| 6,525,009 | B2 | 2/2003 | Sachdev |
| 6,538,057 | B1 | 3/2003 | Wildburg |
| 6,547,867 | B2 | 4/2003 | Rogols |
| 6,555,616 | B1 | 4/2003 | Helbing |
| 6,559,302 | B1 | 5/2003 | Shah |
| 6,562,267 | B1 | 5/2003 | Hansen |
| 6,596,103 | B1 | 7/2003 | Hansen |
| 6,613,378 | B1 | 9/2003 | Erhan |
| 6,638,882 | B1 | 10/2003 | Helbing |
| 6,638,884 | B2 | 10/2003 | Quick |
| 6,699,945 | B1 | 3/2004 | Chen |
| 6,706,853 | B1 | 3/2004 | Stanssens |
| 6,719,862 | B2 | 4/2004 | Quick |
| 6,730,730 | B1 | 5/2004 | Hansen |
| 6,753,361 | B2 | 6/2004 | Kroner |
| 6,818,694 | B2 | 11/2004 | Hindi |
| 6,821,547 | B2 | 11/2004 | Shah |
| 6,852,247 | B2 | 2/2005 | Bytnar |
| 6,858,074 | B2 | 2/2005 | Anderson |
| 6,861,495 | B2 | 3/2005 | Barsotti |
| 6,864,044 | B2 | 3/2005 | Ishikawa |
| 6,878,800 | B2 | 4/2005 | Husemoen |
| 6,884,849 | B2 | 4/2005 | Chen |
| 6,955,844 | B2 | 10/2005 | Tagge |
| 6,962,714 | B2 | 11/2005 | Hei |
| 6,989,171 | B2 | 1/2006 | Portman |
| 6,992,203 | B2 | 1/2006 | Trusovs |
| 7,018,490 | B2 | 3/2006 | Hansen |
| 7,029,717 | B1 | 4/2006 | Ojima |
| 7,067,579 | B2 | 6/2006 | Taylor |
| 7,083,831 | B1 | 8/2006 | Koch |
| 7,090,745 | B2 | 8/2006 | Beckman |
| 7,141,626 | B2 | 11/2006 | Rodrigues |
| 7,144,474 | B1 | 12/2006 | Hansen |
| 7,195,792 | B2 | 3/2007 | Boston |
| 7,201,778 | B2 | 4/2007 | Smith |
| 7,201,825 | B2 | 4/2007 | Dezutter |
| 7,202,326 | B2 | 4/2007 | Kuroda |
| 7,241,487 | B2 | 7/2007 | Taylor |
| 7,458,235 | B2 | 12/2008 | Beaufils |
| 7,514,027 | B2 | 4/2009 | Horres |
| 7,655,711 | B2 | 2/2010 | Swift |
| 7,772,347 | B2 | 8/2010 | Swift |
| 7,795,354 | B2 | 9/2010 | Srinivasan |
| 7,803,879 | B2 | 9/2010 | Srinivasan |
| 7,807,771 | B2 | 10/2010 | Swift |
| 7,842,382 | B2 | 11/2010 | Helbing |
| 7,854,980 | B2* | 12/2010 | Jackson ................. C04B 30/02 |
| 7,883,693 | B2 | 2/2011 | Sehl |
| 7,888,445 | B2 | 2/2011 | Swift |
| 7,947,765 | B2 | 5/2011 | Swift |
| 8,114,210 | B2 | 2/2012 | Hampson |
| 8,182,648 | B2 | 5/2012 | Swift |
| 8,211,923 | B2 | 7/2012 | Wagner |
| 8,377,564 | B2 | 2/2013 | Shooshtari |
| 8,501,838 | B2* | 8/2013 | Jackson ................. B27N 3/002 |
| | | | 524/13 |
| 8,680,224 | B2 | 3/2014 | Zhang |
| 8,691,934 | B2 | 4/2014 | Helbing |
| 8,900,495 | B2 | 12/2014 | Pacorel |
| 8,901,208 | B2* | 12/2014 | Jackson ................. B27N 3/002 |
| | | | 524/13 |
| 9,039,827 | B2* | 5/2015 | Hampson ............. C03C 25/321 |
| | | | 106/217.6 |
| 2001/0017427 | A1 | 8/2001 | Rosthauser |
| 2001/0046824 | A1 | 11/2001 | Nigam |
| 2002/0000100 | A1 | 1/2002 | Burg |
| 2002/0025435 | A1 | 2/2002 | Hansen |
| 2002/0026025 | A1 | 2/2002 | Kuo |
| 2002/0028857 | A1 | 3/2002 | Holy |
| 2002/0032253 | A1 | 3/2002 | Lorenz |
| 2002/0042473 | A1 | 4/2002 | Trollsas |
| 2002/0091185 | A1 | 7/2002 | Taylor |
| 2002/0096278 | A1 | 7/2002 | Foster |
| 2002/0123598 | A1 | 9/2002 | Sieker |
| 2002/0130439 | A1 | 9/2002 | Kroner |
| 2002/0161108 | A1 | 10/2002 | Schultz |
| 2002/0197352 | A1 | 12/2002 | Portman |
| 2003/0005857 | A1 | 1/2003 | Minami |
| 2003/0040239 | A1 | 2/2003 | Toas |
| 2003/0044513 | A1 | 3/2003 | Shah |
| 2003/0066523 | A1 | 4/2003 | Lewis |
| 2003/0071879 | A1 | 4/2003 | Swenson |
| 2003/0116294 | A1 | 6/2003 | Kehrer |
| 2003/0134945 | A1 | 7/2003 | Capps |
| 2003/0148084 | A1 | 8/2003 | Trocino |
| 2003/0153690 | A1 | 8/2003 | Husemoen |
| 2003/0185991 | A1 | 10/2003 | Wigger |
| 2003/0203117 | A1 | 10/2003 | Bartkowiak |

(56) References Cited

U.S. PATENT DOCUMENTS

| | | |
|---|---|---|
| 2004/0002567 A1 | 1/2004 | Chen |
| 2004/0019168 A1 | 1/2004 | Soerens |
| 2004/0024170 A1 | 2/2004 | Husemoen |
| 2004/0033269 A1 | 2/2004 | Hei |
| 2004/0033747 A1 | 2/2004 | Miller |
| 2004/0034154 A1 | 2/2004 | Tutin |
| 2004/0038017 A1 | 2/2004 | Tutin |
| 2004/0048531 A1 | 3/2004 | Belmares |
| 2004/0077055 A1 | 4/2004 | Fosdick |
| 2004/0079499 A1 | 4/2004 | Dezutter |
| 2004/0087024 A1 | 5/2004 | Bellocq |
| 2004/0087719 A1 | 5/2004 | Rautschek |
| 2004/0122166 A1 | 6/2004 | O'Brien-Bernini |
| 2004/0131874 A1 | 7/2004 | Tutin |
| 2004/0144706 A1 | 7/2004 | Beaufils |
| 2004/0152824 A1 | 8/2004 | Dobrowolski |
| 2004/0161993 A1 | 8/2004 | Tripp |
| 2004/0209851 A1 | 10/2004 | Nelson |
| 2004/0213930 A1 | 10/2004 | Halabisky |
| 2004/0220368 A1 | 11/2004 | Li |
| 2004/0249066 A1 | 12/2004 | Heinzman |
| 2004/0254285 A1 | 12/2004 | Rodrigues |
| 2004/0260082 A1 | 12/2004 | Van Der Wilden |
| 2005/0001198 A1 | 1/2005 | Bytnar |
| 2005/0017394 A1 | 1/2005 | Hochsmann |
| 2005/0027283 A1 | 2/2005 | Richard |
| 2005/0033037 A1 | 2/2005 | Trusovs |
| 2005/0048212 A1 | 3/2005 | Clamen |
| 2005/0059770 A1 | 3/2005 | Srinivasan |
| 2005/0082025 A1* | 4/2005 | Carroll .................. C08L 39/04 |
| | | 162/158 |
| 2005/0171085 A1 | 8/2005 | Pinto |
| 2005/0196421 A1 | 9/2005 | Hunter |
| 2005/0202224 A1 | 9/2005 | Helbing |
| 2005/0208852 A1 | 9/2005 | Weber |
| 2005/0215153 A1 | 9/2005 | Cossement |
| 2005/0245669 A1 | 11/2005 | Clungeon |
| 2005/0275133 A1 | 12/2005 | Cabell |
| 2005/0288479 A1 | 12/2005 | Kuroda |
| 2006/0005580 A1 | 1/2006 | Espiard |
| 2006/0044302 A1 | 3/2006 | Chen |
| 2006/0099870 A1 | 5/2006 | Garcia |
| 2006/0111480 A1 | 5/2006 | Hansen |
| 2006/0124538 A1 | 6/2006 | Morcrette |
| 2006/0135433 A1 | 6/2006 | Murray |
| 2006/0141177 A1 | 6/2006 | Ligtenberg |
| 2006/0179892 A1 | 8/2006 | Horres |
| 2006/0188465 A1 | 8/2006 | Perrier |
| 2006/0198954 A1 | 9/2006 | Frechem |
| 2006/0231487 A1 | 10/2006 | Bartley |
| 2006/0252855 A1 | 11/2006 | Pisanova |
| 2006/0281622 A1 | 12/2006 | Maricourt |
| 2007/0006390 A1 | 1/2007 | Clamen |
| 2007/0009582 A1 | 1/2007 | Madsen |
| 2007/0027281 A1 | 2/2007 | Michl |
| 2007/0027283 A1 | 2/2007 | Swift et al. |
| 2007/0039520 A1 | 2/2007 | Crews |
| 2007/0082983 A1 | 4/2007 | Crews |
| 2007/0123679 A1 | 5/2007 | Swift |
| 2007/0123680 A1 | 5/2007 | Swift |
| 2007/0129522 A1 | 6/2007 | Burckhardt |
| 2007/0142596 A1 | 6/2007 | Swift |
| 2007/0158022 A1 | 7/2007 | Heep |
| 2007/0184740 A1 | 8/2007 | Keller |
| 2007/0191574 A1 | 8/2007 | Miller |
| 2007/0270070 A1 | 11/2007 | Othman |
| 2007/0287018 A1 | 12/2007 | Tutin |
| 2007/0292618 A1 | 12/2007 | Srinivasan |
| 2007/0292619 A1 | 12/2007 | Srinivasan |
| 2007/0298274 A1 | 12/2007 | Eriksson |
| 2008/0009209 A1 | 1/2008 | Clamen |
| 2008/0009616 A1 | 1/2008 | Frank |
| 2008/0051539 A1 | 2/2008 | Kelly |
| 2008/0060551 A1 | 3/2008 | Crews |
| 2008/0081138 A1 | 4/2008 | Moore |
| 2008/0108741 A1 | 5/2008 | Van Herwijnen |
| 2008/0160260 A1 | 7/2008 | Wada |
| 2008/0160302 A1 | 7/2008 | Asrar |
| 2008/0194738 A1 | 8/2008 | Crews |
| 2009/0169867 A1 | 7/2009 | Kelly |
| 2009/0170978 A1 | 7/2009 | Kelly |
| 2009/0227732 A1 | 9/2009 | Glockner |
| 2009/0301972 A1 | 12/2009 | Hines |
| 2009/0304919 A1 | 12/2009 | Huenig |
| 2009/0306255 A1 | 12/2009 | Patel |
| 2009/0324915 A1* | 12/2009 | Swift .................. C03C 25/26 |
| | | 428/219 |
| 2010/0029160 A1 | 2/2010 | Srinivasan |
| 2010/0058661 A1 | 3/2010 | Jackson |
| 2010/0080976 A1* | 4/2010 | Jackson .................. C04B 30/02 |
| | | 428/292.1 |
| 2010/0084598 A1* | 4/2010 | Jackson .................. C03C 25/26 |
| | | 252/62 |
| 2010/0086726 A1* | 4/2010 | Jackson .................. C03C 25/321 |
| | | 428/98 |
| 2010/0087571 A1* | 4/2010 | Jackson .................. B27N 3/002 |
| | | 524/13 |
| 2010/0098947 A1 | 4/2010 | Inoue |
| 2010/0117023 A1 | 5/2010 | Dopico |
| 2010/0129640 A1 | 5/2010 | Kelly |
| 2010/0130649 A1 | 5/2010 | Swift |
| 2010/0175826 A1 | 7/2010 | Huenig |
| 2010/0210595 A1 | 8/2010 | Wagner |
| 2010/0222463 A1 | 9/2010 | Brady |
| 2010/0222566 A1 | 9/2010 | Fosdick |
| 2010/0282996 A1 | 11/2010 | Jaffrennou |
| 2010/0301256 A1 | 12/2010 | Hampson |
| 2010/0320113 A1 | 12/2010 | Swift |
| 2011/0021672 A1 | 1/2011 | Crews |
| 2011/0039111 A1 | 2/2011 | Shooshtari |
| 2011/0040010 A1 | 2/2011 | Shooshtari |
| 2011/0042303 A1* | 2/2011 | Shooshtari ............. D04H 1/587 |
| | | 210/508 |
| 2011/0045966 A1 | 2/2011 | Shooshtari |
| 2011/0046271 A1 | 2/2011 | Shooshtari et al. |
| 2011/0089074 A1* | 4/2011 | Jackson .................. C04B 30/02 |
| | | 206/524.1 |
| 2011/0135937 A1 | 6/2011 | Swift |
| 2011/0190425 A1* | 8/2011 | Swift .................. C08J 5/04 |
| | | 524/35 |
| 2011/0220835 A1 | 9/2011 | Swift |
| 2011/0256790 A1 | 10/2011 | Toas |
| 2011/0260094 A1 | 10/2011 | Hampson |
| 2011/0262648 A1 | 10/2011 | Lee |
| 2011/0263757 A1 | 10/2011 | Rand |
| 2011/0306726 A1 | 12/2011 | Bailey |
| 2012/0133073 A1* | 5/2012 | Pacorel .................. C08F 8/14 |
| | | 264/128 |
| 2012/0135152 A1* | 5/2012 | Finch .................. C08J 5/24 |
| | | 427/389.9 |
| 2012/0156954 A1 | 6/2012 | Eckert |
| 2013/0029150 A1 | 1/2013 | Appley |
| 2013/0032749 A1* | 2/2013 | Jaffrennou ............. C03C 25/321 |
| | | 252/62 |
| 2013/0047888 A1* | 2/2013 | Mueller .................. C08G 12/00 |
| | | 106/163.01 |
| 2013/0059075 A1* | 3/2013 | Appley .................. C08G 12/00 |
| | | 427/222 |
| 2013/0082205 A1 | 4/2013 | Mueller |
| 2013/0127085 A1* | 5/2013 | Kalbe .................. C09D 105/00 |
| | | 264/134 |
| 2013/0133548 A1* | 5/2013 | Shooshtari ............. C08K 7/14 |
| | | 106/18.31 |
| 2013/0174758 A1* | 7/2013 | Mueller .................. C08K 7/04 |
| | | 106/162.9 |
| 2013/0234362 A1 | 9/2013 | Swift |
| 2013/0236650 A1 | 9/2013 | Swift |
| 2013/0237113 A1 | 9/2013 | Swift |
| 2013/0244524 A1 | 9/2013 | Swift |
| 2014/0091247 A1 | 4/2014 | Jackson |
| 2014/0116291 A1* | 5/2014 | Jackson .................. B27N 3/002 |
| | | 106/164.01 |

(56) References Cited

U.S. PATENT DOCUMENTS

| | | | | |
|---|---|---|---|---|
| 2014/0134909 A1* | 5/2014 | Guo | C09J 101/28 | 442/331 |
| 2014/0186635 A1* | 7/2014 | Mueller | C08G 12/00 | 428/426 |
| 2014/0312260 A2* | 10/2014 | Hampson | C03C 25/321 | 252/62 |
| 2014/0323618 A1* | 10/2014 | Appley | C08G 12/00 | 524/14 |
| 2014/0357787 A1* | 12/2014 | Jobber | C08G 8/00 | 524/596 |
| 2015/0010949 A1* | 1/2015 | Jackson | C08L 79/02 | 435/84 |
| 2015/0203399 A1* | 7/2015 | Didier | C03C 25/26 | 428/426 |
| 2015/0224671 A1* | 8/2015 | Hand | B27N 3/00 | 428/533 |
| 2015/0267055 A1* | 9/2015 | Jackson | B27N 3/002 | 106/162.5 |
| 2015/0299391 A1* | 10/2015 | Pacorel | D04H 1/587 | 427/385.5 |
| 2015/0315339 A1* | 11/2015 | Pacorel | C08G 73/0206 | 536/55 |
| 2017/0002971 A1* | 1/2017 | Hampson | C03C 25/321 | |
| 2017/0015694 A1* | 1/2017 | Mueller | C08G 12/00 | |
| 2017/0037187 A1* | 2/2017 | Appley | C08G 12/00 | |

FOREIGN PATENT DOCUMENTS

| | | |
|---|---|---|
| CA | 1090026 | 11/1980 |
| CA | 2037214 | 9/1991 |
| CA | 2232334 | 11/1998 |
| CA | 2458333 | 12/1999 |
| CA | 2278946 | 1/2000 |
| CA | 2470783 | 12/2004 |
| CN | 1251738 | 5/2000 |
| DE | 1905054 | 8/1969 |
| DE | 4142261 | 6/1993 |
| DE | 4233622 | 4/1994 |
| DE | 4308089 | 9/1994 |
| DE | 102004033561 | 9/2005 |
| DE | 102005023431 | 11/2006 |
| EP | 0044614 A2 | 1/1982 |
| EP | 0099801 | 2/1984 |
| EP | 354023 | 2/1990 |
| EP | 0461995 | 12/1991 |
| EP | 0524518 A2 | 1/1993 |
| EP | 0547819 A2 | 6/1993 |
| EP | 0583086 A1 | 2/1994 |
| EP | 0714754 A2 | 6/1996 |
| EP | 796681 | 9/1997 |
| EP | 0826710 A2 | 3/1998 |
| EP | 856494 | 8/1998 |
| EP | 0873976 A1 | 10/1998 |
| EP | 878135 | 11/1998 |
| EP | 0882756 A2 | 12/1998 |
| EP | 0911361 A1 | 4/1999 |
| EP | 915811 | 5/1999 |
| EP | 936060 | 8/1999 |
| EP | 976866 | 2/2000 |
| EP | 0990729 A1 | 4/2000 |
| EP | 1038433 A1 | 9/2000 |
| EP | 1193288 A1 | 4/2002 |
| EP | 1084167 | 9/2002 |
| EP | 1268702 | 1/2003 |
| EP | 1382642 | 1/2004 |
| EP | 1486547 A2 | 12/2004 |
| EP | 1522642 | 4/2005 |
| EP | 1698598 A1 | 9/2006 |
| EP | 1767566 | 4/2007 |
| EP | 2223941 | 9/2010 |
| EP | 2253663 | 11/2010 |
| FR | 2614388 | 10/1988 |
| GB | 809675 | 3/1959 |
| GB | 926749 | 5/1963 |
| GB | 1391172 | 4/1975 |
| GB | 1469331 | 4/1977 |
| GB | 1512066 | 5/1978 |
| GB | 1525541 | 9/1978 |
| GB | 2047258 | 11/1980 |
| GB | 2078805 A | 1/1982 |
| GB | 2173523 | 10/1986 |
| GB | 2251438 | 7/1992 |
| JP | 53113784 | 10/1978 |
| JP | 57101100 | 6/1982 |
| JP | 5811193 | 1/1983 |
| JP | 61195647 | 8/1986 |
| JP | 3-173680 | 7/1991 |
| JP | 05186635 | 7/1993 |
| JP | 7-034023 | 2/1995 |
| JP | 09157627 | 6/1997 |
| JP | 10234314 | 9/1998 |
| JP | 11035491 | 2/1999 |
| JP | 11181690 | 7/1999 |
| JP | 2000327841 | 11/2000 |
| JP | 2002293576 | 9/2002 |
| JP | 2003147276 | 5/2003 |
| JP | 2003238921 | 8/2003 |
| JP | 2004060058 | 2/2004 |
| JP | 2005306919 | 11/2005 |
| NZ | 549563 | 1/2008 |
| RU | 1765996 | 8/1995 |
| SU | 374400 | 3/1973 |
| WO | 1990007541 | 7/1990 |
| WO | 1992012198 | 7/1992 |
| WO | 1995034517 | 12/1995 |
| WO | 1997049646 | 12/1997 |
| WO | 1999036368 | 7/1999 |
| WO | 199947765 | 9/1999 |
| WO | 199960042 | 11/1999 |
| WO | 199960043 | 11/1999 |
| WO | 200058085 | 10/2000 |
| WO | 2001014491 | 3/2001 |
| WO | 2001059026 | 8/2001 |
| WO | 200200429 | 1/2002 |
| WO | 2003029496 | 4/2003 |
| WO | 2003071879 | 9/2003 |
| WO | 2003106561 | 12/2003 |
| WO | 2004076734 | 9/2004 |
| WO | 2005087837 | 9/2005 |
| WO | 2006044302 | 4/2006 |
| WO | 2006136614 | 12/2006 |
| WO | 2007014236 | 2/2007 |
| WO | 2007024020 A1 | 3/2007 |
| WO | 2007050964 | 5/2007 |
| WO | 2007112335 | 10/2007 |
| WO | 2008089847 | 7/2008 |
| WO | 2008089851 | 7/2008 |
| WO | 2008141201 | 11/2008 |
| WO | 2009019235 A1 | 2/2009 |
| WO | 2010139899 | 12/2010 |
| WO | 2011019590 | 2/2011 |
| WO | 2011019593 | 2/2011 |
| WO | 2011019597 | 2/2011 |
| WO | 2011019598 | 2/2011 |
| WO | 2011022224 | 2/2011 |
| WO | 2011022226 | 2/2011 |
| WO | 2011022227 | 2/2011 |
| WO | 2011138458 A1 | 11/2011 |
| WO | 2011138459 | 11/2011 |
| WO | 2013150123 | 10/2013 |

OTHER PUBLICATIONS

First Response to the Written Opinion of the International Preliminary Examination Authority (WOIPEA) for PCT Application No. PCT/EP2013/057151, dated Jul. 7, 2014, 3 pages.

Additional Response to the Written Opinion of the International Preliminary Examination Authority (WOIPEA) for PCT Application No. PCT/EP2013/057151, dated Jul. 24, 2014, 18 pages.

Office action for co-pending U.S. Appl. No. 14/390,445 (14 pages)—dated Dec. 3, 2015.

Office action for co-pending U.S. Appl. No. 15/172,432 (16 pages)—dated Apr. 17, 2017.

(56) References Cited

OTHER PUBLICATIONS

International Search Report and Written Opinion for PCT/US2008/059730, completed Sep. 22, 2008.
International Search Report and Written Opinion for PCT/US2008/069046, completed Sep. 25, 2008.
International Search Report for PCT/EP2008/060185, completed Oct. 23, 2008.
International Search Report for PCT/EP2011/057363, completed Sep. 5, 2011.
Ames, J.M., "The Maillard Browning Reaction—an Update,"Chemistry & Industry, No. 17, 1988, 4 pages.
"Gamma-aminopropyltrimethoxysilane," Hawley's Condensed Chemical Dictionary, 14th Edition, John Wiley & Sons, Inc., 2002, 1 page.
Hodge, J.E., Chemistry of Browning Reactions in Model Systems, 1953, J. Agric. Food Chem., vol. 1, No. 15, pp. 928-943.
Agyei-Aye et al., "The Role of Anion in the Reaction of Reducing Sugars with Ammonium Salts," Carbohydrate Research 2002, 337: 2273-2277.
Laroque et al., "Kinetic study on the Maillard reaction. Consideration of sugar reactivity," Food Chemistry 2008, 111: 1032-1042.
Bjorksten et al., "Polyester Resin—Glass Fiber Laminates," Industrial and Engineering Chemistry (1954).
Dow Corning, "A Guide to Silane Solutions," 2005.
Knauf Data Sheet, 2006.
Molasses Corporation, United States Sugar Corporation, http://www.suga-lik.com/molasses/composition.html (Sep. 29, 2003).
Clamen, Guy, "Acrylic Thermosets: A Safe Alternative to Formaldehyde Resins," Nonwovens World, Apr.-May 2004, pp. 96-102.
Opposition to AU 2006272595, Amended Statement of Grounds and Particulars, issued from Australian Patent Office, Jul. 6, 2012, 22 pages.
Decision re Opposition to AU 2006272595, issued from Australian Patent Office, Aug. 14, 2015, 25 pages.
Opposition to EP 1732968, Notice of Opposition: Prior Art, Scope of the Patent, Reasons for the Opposition, issued from European Patent Office, Mar. 8, 2012, 18 pages.
Decision re Opposition to EP 1732968, issued from the European Patent Office, Nov. 14, 2014, 5 pages.
Opposition to EA 019802, submitted to Eurasian Patent Office on Dec. 26, 2014, 36 pages.
Decision re Opposition to EA 019802, issued by Eurasian Patent Office on Aug. 18, 2015, 15 pages.
Owens Corning Retiree Update: What Goes Around, Comes Around: A tale of Natural Binders, revised Mar. 20, 2013 p. 4.
A.P. Bryant, "The Terminology of Sugars," Industrial and Engineering Chemistry, vol. 26, No. 2, p. 231, Feb. 1934.
Food Flavor Chemistry, p. 162, Mar. 21, 2009 (English Abstract).
Office action for co-pending U.S. Appl. No. 12/524,502 (9 pages)—dated Sep. 21, 2012.
Office action for co-pending U.S. Appl. No. 12/524,502 (9 pages)—dated Apr. 4, 2013.
Office action for co-pending U.S. Appl. No. 12/524,512 (7 pages)—dated Aug. 6, 2012.
Office action for co-pending U.S. Appl. No. 12/524,512 (9 pages)—dated Apr. 1, 2013.
Office action for co-pending U.S. Appl. No. 12/524,512 (14 pages)—dated Nov. 12, 2014.
Office action for co-pending U.S. Appl. No. 12/524,512 (9 pages)—dated Jul. 10, 2015.
Office action for co-pending U.S. Appl. No. 12/524,512 (10 pages)—dated Mar. 23, 2016.
Office action for co-pending U.S. Appl. No. 12/524,512 (13 pages)—dated Oct. 5, 2016.
Office action for co-pending U.S. Appl. No. 12/524,512 (13 pages)—dated Apr. 6, 2018.
Office action for co-pending U.S. Appl. No. 12/524,469 (7 pages)—dated Jun. 7, 2012.
Office action for co-pending U.S. Appl. No. 12/524,469 (8 pages)—dated Jan. 29, 2013.
Office action for co-pending U.S. Appl. No. 12/524,469 (7 pages)—dated Aug. 20, 2013.
Office action for co-pending U.S. Appl. No. 12/524,469 (9 pages)—dated Jun. 9, 2014.
Office action for co-pending U.S. Appl. No. 12/524,469 (9 pages)—dated Oct. 17, 2014.
Office action for co-pending U.S. Appl. No. 12/524,469 (9 pages)—dated Jul. 23, 2015.
Office action for co-pending U.S. Appl. No. 12/524,539 (13 pages)—dated Jun. 21, 2012.
Office action for co-pending U.S. Appl. No. 12/524,539 (13 pages)—dated Jun. 6, 2013.
Office action for co-pending U.S. Appl. No. 12/524,539 (12 pages)—dated Dec. 17, 2014.
Office action for co-pending U.S. Appl. No. 12/524,539 (7 pages)—dated Jul. 15, 2015.
Office action for co-pending U.S. Appl. No. 12/524,539 (7 pages)—dated Mar. 23, 2016.
Office action for co-pending U.S. Appl. No. 12/524,539 (7 pages)—dated Dec. 29, 2016.
Office action for co-pending U.S. Appl. No. 12/524,522 (4 pages)—dated Oct. 11, 2011.
Office action for co-pending U.S. Appl. No. 12/667,718 (5 pages)—dated Sep. 3, 2013.
Office action for co-pending U.S. Appl. No. 12/667,718 (6 pages)—dated Sep. 9, 2014.
Office action for co-pending U.S. Appl. No. 12/671,922 (10 pages)—dated Oct. 7, 2011.
Office action for co-pending U.S. Appl. No. 12/671,922 (10 pages)—dated May 10, 2012.
Office action for co-pending U.S. Appl. No. 12/671,922 (9 pages)—dated Sep. 23, 2014.
Office action for co-pending U.S. Appl. No. 12/671,922 (5 pages)—dated Apr. 4, 2016.
Office action for co-pending U.S. Appl. No. 13/388,408 (5 pages)—dated Aug. 15, 2013.
Office action for co-pending U.S. Appl. No. 13/371,829 (9 pages)—dated Dec. 20, 2012.
Office action for co-pending U.S. Appl. No. 13/371,829 (6 pages)—dated Jul. 12, 2013.
Office action for co-pending U.S. Appl. No. 13/371,829 (6 pages)—dated Aug. 12, 2014.
Office action for co-pending U.S. Appl. No. 13/637,794 (8 pages)—dated Aug. 12, 2013.
Office action for co-pending U.S. Appl. No. 13/637,794 (9 pages)—dated Mar. 26, 2014.
Office action for co-pending U.S. Appl. No. 13/696,439 (11 pages)—dated Jan. 8, 2014.
Office action for co-pending U.S. Appl. No. 13/696,452 (7 pages)—dated Jan. 13, 2015.
Office action for co-pending U.S. Appl. No. 13/696,452 (9 pages)—dated Oct. 27, 2015.
Office action for co-pending U.S. Appl. No. 13/702,144 (6 pages)—dated Jan. 10, 2014.
Office action for co-pending U.S. Appl. No. 13/702,144 (7 pages)—dated Jul. 29, 2014.
Office action for co-pending U.S. Appl. No. 13/823,818 (9 pages)—dated Mar. 26, 2015.
Office action for co-pending U.S. Appl. No. 13/866,368 (16 pages)—dated Aug. 29, 2013.
Office action for co-pending U.S. Appl. No. 13/866,368 (11 pages)—dated Apr. 16, 2014.
Office action for co-pending U.S. Appl. No. 13/866,368 (8 pages)—dated Aug. 21, 2014.
Office action for co-pending U.S. Appl. No. 13/866,419 (14 pages)—dated Sep. 20, 2013.
Office action for co-pending U.S. Appl. No. 13/866,419 (10 pages)—dated Apr. 25, 2014.
Office action for co-pending U.S. Appl. No. 13/866,419 (8 pages)—dated Oct. 9, 2014.
Office action for co-pending U.S. Appl. No. 13/866,419 (8 pages)—dated Sep. 25, 2015.

(56) References Cited

OTHER PUBLICATIONS

Office action for co-pending U.S. Appl. No. 13/868,233 (23 pages)—dated Aug. 13, 2013.
Office action for co-pending U.S. Appl. No. 13/868,233 (12 pages)—dated Apr. 15, 2014.
Office action for co-pending U.S. Appl. No. 13/868,233 (8 pages)—dated Oct. 7, 2014.
Office action for co-pending U.S. Appl. No. 13/868,233 (8 pages)—dated Jul. 16, 2015.
Office action for co-pending U.S. Appl. No. 13/868,238 (8 pages)—dated Jul. 16, 2014.
Office action for co-pending U.S. Appl. No. 12/976,379 (7 pages)—dated Jan. 10, 2012.
Office action for co-pending U.S. Appl. No. 12/976,379 (6 pages)—dated Jul. 27, 2012.
Office action for co-pending U.S. Appl. No. 12/976,379 (9 pages)—dated Mar. 7, 2013.
Office action for co-pending U.S. Appl. No. 12/976,379 (8 pages)—dated Aug. 20, 2013.
Office action for co-pending U.S. Appl. No. 12/599,858 (8 pages)—dated May 11, 2011.
Office action for co-pending U.S. Appl. No. 13/341,542 (8 pages)—dated Dec. 26, 2012.
Office action for co-pending U.S. Appl. No. 13/341,542 (7 pages)—dated Feb. 10, 2014.
Office action for co-pending U.S. Appl. No. 14/026,394 (6 pages)—dated Aug. 14, 2014.
Office action for co-pending U.S. Appl. No. 14/272,556 (14 pages)—dated Nov. 20, 2014.
Office action for co-pending U.S. Appl. No. 14/272,556 (12 pages)—dated Sep. 17, 2015.
Office action for co-pending U.S. Appl. No. 14/342,069 (17 pages)—dated Dec. 29, 2015.
Office action for co-pending U.S. Appl. No. 14/342,069 (22 pages)—dated Sep. 2, 2016.
Office action for co-pending U.S. Appl. No. 14/342,069 (21 pages)—dated Sep. 26, 2017.
Office action for co-pending U.S. Appl. No. 14/342,069 (21 pages)—dated Jun. 6, 2018.
Office action for co-pending U.S. Appl. No. 14/649,277 (9 pages)—dated Jul. 22, 2016.
Office action for co-pending U.S. Appl. No. 14/686,915 (8 pages)—dated Nov. 18, 2016.
Office action for co-pending U.S. Appl. No. 14/810,765 (7 pages)—dated Jan. 29, 2016.
Office action for co-pending U.S. Appl. No. 14/828,916 (8 pages)—dated Nov. 25, 2016.
Office action for co-pending U.S. Appl. No. 14/867,502 (9 pages)—dated Nov. 18, 2016.
Office action for co-pending U.S. Appl. No. 15/702,087 (5 pages)—dated Nov. 9, 2018.
Office action for co-pending U.S. Appl. No. 15/177,442 (17 pages)—dated May 19, 2017.
Office action for co-pending U.S. Appl. No. 15/378,159 (18 pages)—dated Mar. 2, 2017.
Office action for co-pending U.S. Appl. No. 15/222,122 (8 pages)—dated Nov. 20, 2017.
Office action for co-pending U.S. Appl. No. 15/310,837 (13 pages)—dated Jun. 21, 2018.
Office action for co-pending U.S. Appl. No. 15/411,972 (9 pages)—dated Mar. 28, 2017.
Office action for co-pending U.S. Appl. No. 15/411,972 (8 pages)—dated Nov. 29, 2017.
Office action for co-pending U.S. Appl. No. 15/411,972 (9 pages)—dated Jun. 14, 2018.
Office action for co-pending U.S. Appl. No. 15/116,254 (8 pages)—dated Apr. 26, 2018.
Office action for co-pending U.S. Appl. No. 15/116,254 (10 pages)—dated Aug. 15, 2018.
Other Information—Narrative of verbal disclosure of Brian Swift (1 page)—May 13, 2014.
Petition for Inter Partes Review of U.S. Pat. No. 8,114,210 (52 pages, filed Jun. 12, 2015 by Petitioners Johns Manville Corporation and Johns Manville, Inc.).
Declaration of Dr. Frederick J. Hirsekorn Regarding U.S. Pat. No. 8,114,210 (58 pages, filed Jun. 12, 2015 by Petitioners Johns Manville Corporation and Johns Manville, Inc. in connection with Petition for Inter Partes Review of U.S. Pat. No. 8,114,210).
1st Petition for Inter Partes Review of U.S. Pat. No. D631,670 (68 pages, filed Jun. 19, 2015 by Petitioners Johns Manville Corporation and Johns Manville, Inc.).
2nd Petition for Inter Partes Review of U.S. Pat. No. D631,670 (62 pages, filed Nov. 2, 2015 by Petitioners Johns Manville Corporation and Johns Manville, Inc.).
Decision of PTAB regarding Institution of Inter Partes Review for U.S. Pat. No. D631,670 (33 pages)—Jan. 12, 2016.
Decision2 of PTAB regarding Institution of Inter Partes Review for U.S. Pat. No. D631,670 (27 pages)—May 9, 2016.
Final Written Decision of PTAB regarding Inter Partes Review of U.S. Pat. No. D631,670 based on 1st Petition (56 pages)—Jan. 11, 2017.
Final Written Decision of PTAB regarding Inter Partes Review of U.S. Pat. No. D631,670 based on 2nd Petition (55 pages)—May 8, 2017.
Court of Appeals for Federal Circuit Judgment from Appeal of PTAB Decisions in Inter Partes Reviews of U.S. Pat. No. D631,670 (2 pages)—Jul. 13, 2018.
1st Petition for Inter Partes Review of U.S. Pat. No. 8,940,089 (61 pages, filed Jul. 1, 2015 by Petitioners Johns Manville Corporation and Johns Manville, Inc.).
Declaration of Dr. Frederick J. Hirsekorn Regarding U.S. Pat. No. 8,940,089 (70 pages, filed Jul. 1, 2015 by Petitioners Johns Manville Corporation and Johns Manville, Inc. in connection with 1st Petition for Inter Partes Review of U.S. Pat. No. 8,940,089).
2nd Petition for Inter Partes Review of U.S. Pat. No. 8,940,089 (56 pages, filed Jul. 10, 2015 by Petitioners Johns Manville Corporation and Johns Manville, Inc.).
Declaration of Dr. Frederick J. Hirsekorn Regarding U.S. Pat. No. 8,940,089 (67 pages, filed Jul. 10, 2015 by Petitioners Johns Manville Corporation and Johns Manville, Inc. in connection with 2nd Petition for Inter Partes Review of U.S. Pat. No. 8,940,089).
3rd Petition for Inter Partes Review of U.S. Pat. No. 8,940,089 (62 pages, filed Jul. 17, 2015 by Petitioners Johns Manville Corporation and Johns Manville, Inc.).
Declaration of Dr. Frederick J. Hirsekorn Regarding U.S. Pat. No. 8,940,089 (76 pages, filed Jul. 17, 2015 by Petitioners Johns Manville Corporation and Johns Manville, Inc. in connection with 3rd Petition for Inter Partes Review of U.S. Pat. No. 8,940,089).
Declaration of Dr. Elam Leed (11 pages, filed Jul. 1, Jul. 10, and Jul. 17, 2015 by Petitioners Johns Manville Corporation and Johns Manville, Inc. in connection with 1st, 2nd and 3rd Petition for Inter Partes Review of U.S. Pat. No. 8,940,089, respectively).
Declaration of Dr. Jonathan Vickers (10 pages, filed Jul. 1, Jul. 10, and Jul. 17, 2015 by Petitioners Johns Manville Corporation and Johns Manville, Inc. in connection with 1st, 2nd and 3rd Petition for Inter Partes Review of U.S. Pat. No. 8,940,089, respectively).
1st Petition for Inter Partes Review of U.S. Pat. No. 9,039,827 (60 pages, filed Jul. 29, 2015 by Petitioners Johns Manville Corporation and Johns Manville, Inc.).
Declaration of Dr. Frederick J. Hirsekorn Regarding U.S. Pat. No. 9,039,827 (72 pages, filed Jul. 29, 2015 by Petitioners Johns Manville Corporation and Johns Manville, Inc. in connection with $1^{st}$ Petition for Inter Partes Review of U.S. Pat. No. 9,039,827).
2nd Petition for Inter Partes Review of U.S. Pat. No. 9,039,827 (51 pages, filed Aug. 5, 2015 by Petitioners Johns Manville Corporation and Johns Manville, Inc.).
Declaration of Dr. Frederick J. Hirsekorn Regarding U.S. Pat. No. 9,039,827 (65 pages, filed Aug. 5, 2015 by Petitioners Johns Manville Corporation and Johns Manville, Inc. in connection with $2^{nd}$ Petition for Inter Partes Review of U.S. Pat. No. 9,039,827).

(56) References Cited

OTHER PUBLICATIONS

3rd Petition for Inter Partes Review of U.S. Pat. No. 9,039,827 (57 pages, filed Aug. 7, 2015 by Petitioners Johns Manville Corporation and Johns Manville, Inc.).
Declaration of Dr. Frederick J. Hirsekorn Regarding U.S. Pat. No. 9,039,827 (75 pages, filed Aug. 7, 2015 by Petitioners Johns Manville Corporation and Johns Manville, Inc. in connection with $3^{rd}$ Petition for Inter Partes Review of U.S. Pat. No. 9,039,827).
Declaration of Dr. Elam Leed (11 pages, filed Jul. 29, Aug. 5, and Aug. 7, 2015 by Petitioners Johns Manville Corporation and Johns Manville, Inc. in connection with 1st, 2nd and 3rd Petition for Inter Partes Review of U.S. Pat. No. 9,039,827, respectively).
Declaration of Dr. Jonathan Vickers (10 pages, filed Jul. 29, Aug. 5, and Aug. 7, 2015 by Petitioners Johns Manville Corporation and Johns Manville, Inc. in connection with 1st, 2nd and 3rd Petition for Inter Partes Review of U.S. Pat. No. 9,039,827, respectively).
Petition for Inter Partes Review of U.S. Pat. No. 9,469,747 (67 pages, filed Mar. 20, 2018 by Petitioners Johns Manville Corporation and Johns Manville, Inc.).
Petition for Inter Partes Review of U.S. Pat. No. 9,828,287 (86 pages, filed Mar. 23, 2018 by Petitioners Johns Manville Corporation and Johns Manville, Inc.).
Petition for Inter Partes Review of U.S. Pat. No. 9,464,207 (78 pages, filed Mar. 28, 2018 by Petitioners Johns Manville Corporation and Johns Manville, Inc.).
Petition for Inter Partes Review of U.S. Pat. No. 9,926,464 (74 pages, filed Mar. 30, 2018 by Petitioners Johns Manville Corporation and Johns Manville, Inc.).
Final Rejection in Ex Parte Reexamination of U.S. Pat. No. 7,888,445 (20 pages)—Jul. 24, 2015.
Final Rejection in Ex Parte Reexamination of U.S. Pat. No. 7,772,347 (23 pages)—Jul. 24, 2015.
Final Rejection in Ex Parte Reexamination of U.S. Pat. No. 7,854,980 (31 pages)—Aug. 18, 2015.
Advisory Action in Ex Parte Reexamination of U.S. Pat. No. 7,888,445 (4 pages)—dated Oct. 6, 2015.
Advisory Action in Ex Parte Reexamination of U.S. Pat. No. 7,772,347 (4 pages)—Oct. 6, 2015.
Advisory Action in Ex Parte Reexamination of U.S. Pat. No. 7,854,980 (4 pages)—dated Nov. 18, 2015.
Examiner's Answer in Ex Parte Reexamination of U.S. Pat. No. 7,888,445 (8 pages)—dated Mar. 23, 2016.
Examiner's Answer in Ex Parte Reexamination of U.S. Pat. No. 7,772,347 (8 pages)—dated Mar. 23, 2016.
Examiner's Answer in Ex Parte Reexamination of U.S. Pat. No. 7,854,980 (8 pages)—dated Mar. 22, 2016.
Decision of PTAB in Ex Parte Reexamination of U.S. Pat. No. 7,888,445 (17 pages)—Sep. 29, 2016.
Decision of PTAB in Ex Parte Reexamination of U.S. Pat. No. 7,772,347 (18 pages)—Sep. 29, 2016.
Decision of PTAB in Ex Parte Reexamination of U.S. Pat. No. 7,854,980 (22 pages)—Sep. 30, 2016.
Court of Appeals for Federal Circuit Judgment from Consolidated Appeal of PTAB Decisions in Ex Parte Reexamination of U.S. Pat. Nos. 7,888,445, 7,772,347 and 7,854,980 (5 pages)—Mar. 9, 2018.
Decision of PTAB in Inter Partes Reexamination of U.S. Pat. No. 7,888,445 (34 pages)—May 1, 2015.
Decision of PTAB in Inter Partes Reexamination of U.S. Pat. No. 7,772,347 (36 pages)—May 1, 2015.
Decision of PTAB in Inter Partes Reexamination of U.S. Pat. No. 7,854,980 (25 pages)—Jul. 30, 2015.
Remand Order of PTAB in Inter Partes Reexamination of U.S. Pat. No. 7,888,445 (5 pages)—Dec. 9, 2015.
Remand Order of PTAB in Inter Partes Reexamination of U.S. Pat. No. 7,772,347 (5 pages)—Dec. 9 , 2015.
Examiner's Determination on Patent Owner Response/Requester Comments after Board Decision in Intern Partes Reexamination of U.S. Pat. No. 7,888,445 (22 pages)—Oct. 17, 2016.
Examiner's Determination on Patent Owner Response/Requester Comments after Board Decision in Intern Partes Reexamination of U.S. Pat. No. 7,772,347 (17 pages)—Oct. 17, 2016.
Court of Appeals for Federal Circuit Opinion/Judgment from Appeal of PTAB Decision in Inter Partes Reexamination of U.S. Pat. No. 7,854,980 (13 pages)—Feb. 27, 2017.
Final Decision of PTAB in Inter Partes Reexamination of U.S. Pat. No. 7,888,445 (25 pages)—Sep. 8, 2017.
Final Decision of PTAB in Inter Partes Reexamination of U.S. Pat. No. 7,772,347 (24 pages)—Sep. 8, 2017.
Decision of PTAB re Request for Rehearing in Inter Partes Reexamination of U.S. Pat. No. 7,888,445 (7 pages)—Feb. 12, 2018.
Decision of PTAB re Request for Rehearing in Inter Partes Reexamination of U.S. Pat. No. 7,772,347 (7 pages)—Feb. 12, 2018.
Decision of PTAB regarding Institution of Inter Partes Review for U.S. Pat. No. 8,114,210 (20 pages)—Oct. 21, 2015.
Final Written Decision of PTAB regarding Inter Partes Review of U.S. Pat. No. 8,114,210 (39 pages)—Oct. 19, 2016.
Court of Appeals for Federal Circuit Judgment from Appeal of PTAB Decision in Inter Partes Review of U.S. Pat. No. 8,114,210 (5 pages)—Jan. 16, 2018.
Decision1 of PTAB declining Institution of Inter Partes Review for U.S. Pat. No. 8,940,089 (16 pages)—Dec. 17, 2015.
Decision2 of PTAB declining Institution of Inter Partes Review for U.S. Pat. No. 8,940,089 (19 pages)—Dec. 17, 2015.
Decision3 of PTAB declining Institution of Inter Partes Review for U.S. Pat. No. 8,940,089 (14 pages)—Dec. 17, 2015.
Decision1 of PTAB declining Institution of Inter Partes Review for U.S. Pat. No. 9,039,827 (16 pages)—Jan. 4, 2016.
Decision2 of PTAB declining Institution of Inter Partes Review for U.S. Pat. No. 9,039,827 (19 pages)—Jan. 4, 2016.
Decision3 of PTAB declining Institution of Inter Partes Review for U.S. Pat. No. 9,039,827 (14 pages)—Jan. 4, 2016.
Decision of PTAB denying Institution of Inter Partes Review for U.S. Pat. No. 9,926,464 (29 pages)—Oct. 2, 2018.
Decision of PTAB denying Institution of Inter Partes Review for U.S. Pat. No. 9,464,207 (28 pages)—Oct. 2, 2018.
Decision of PTAB denying Institution of Inter Partes Review for U.S. Pat. No. 9,469,747 (29 pages)—Oct. 3, 2018.
Decision of PTAB denying Institution of Inter Partes Review for U.S. Pat. No. 9,828,287 (22 pages)—Oct. 16, 2018.
Statement of Revocation Grounds re GB2496951—Claimant Rockwool International (May 21, 2018, 22 pages).
Statement of Revocation Grounds re GB2451719—Claimant Rockwool International (May 18, 2018, 22 pages).
Expert Report re Revocation of GB2451719 and GB2496951—Claimant Rockwool International (Nov. 12, 2018, 11 pages).
Re U.S. Pat. No. 2,965,504—Part 1 (10 pages).
Re U.S. Pat. No. 2,965,504—Part 2 (14 pages).
Re U.S. Pat. No. 2,965,504—Part 3 (14 pages).
Gogek Attorney Comments re U.S. Pat. No. 2,965,504—Apr. 6, 1960 (3 pages).
Gogek Affidavit Under Rule 132 re U.S. Pat. No. 2,965,504—Feb. 26, 1960 (3 pages).
Office action for co-pending U.S. Appl. No. 12/524,512 (15 pages)—dated Jan. 17, 2019.
Decision of USPTO to Reopen Prosecution in Ex Parte Reexamination of U.S. Pat. No. 7,854,980 (7 pages)—Jan. 7, 2019.
Ex Parte Reexamination Certificate for U.S. Pat. No. 7,888,445 (2 pages)—Jan. 9, 2019.

\* cited by examiner

GWST and GWE2 : 324 hrs

Molecular size reference chromatogram of sucrose and different pullulans

BINDERS AND ASSOCIATED PRODUCTS

CROSS-REFERENCE TO RELATED APPLICATIONS

This application is a continuation of U.S. application Ser. No. 15/172,432, filed Jun. 3, 2016, which is a continuation of U.S. application Ser. No. 14/390,445 (now abandoned), filed Oct. 3, 2014, which is a U.S. national counterpart application of International Application Serial No. PCT/EP2013/057151, filed Apr. 4, 2013, under 35 U.S.C. § 371, which claims priority to GB Application Serial No. 1206193.3, filed Apr. 5, 2012, the entire disclosures of each of which are hereby incorporated by reference herein.

TECHNICAL FIELD

The present invention relates to a water-soluble pre-reacted binder composition, a method of its manufacture, a use of said pre-reacted binder composition, a method of manufacturing a collection of matter bound by a polymeric binder, a binder solution or dispersion comprising said pre-reacted binder composition, as well as products comprising the pre-reacted binder composition in a cured state.

BACKGROUND

Generally, binders are useful in fabricating articles because they are capable of consolidating non- or loosely-assembled matter. For example, binders enable two or more surfaces to become united. In particular, binders may be used to produce products comprising consolidated fibers. Thermosetting binders may be characterized by being transformed into insoluble and infusible materials by means of either heat or catalytic action. Examples of a thermosetting binder include a variety of phenol-aldehyde, urea-aldehyde, melamine-aldehyde, and other condensation-polymerization materials like furane and polyurethane resins. Binder compositions containing phenol-aldehyde, resorcinol-aldehyde, phenol/aldehyde/urea, phenol/melamine/aldehyde, and the like are widely used for the bonding of fibers, textiles, plastics, rubbers, and many other materials.

The mineral wool and wood board industries have historically used a phenol formaldehyde based binder, generally extended with urea. Phenol formaldehyde type binders provide suitable properties to the final products; however, desires for greater sustainability and environmental considerations have motivated the development of alternative binders. One such alternative binder is a carbohydrate based binder derived from reacting a carbohydrate and an acid, for example, U.S. Published Application No. 2007/0027283 and Published PCT Application WO2009/019235. Another alternative binder is the esterification products of reacting a polycarboxylic acid and a polyol, for example, U.S. Published Application No. 2005/0202224. Because these binders do not utilize formaldehyde as a reagent, they have been collectively referred to as formaldehyde-free binders.

One area of current development is to find a replacement for the phenol formaldehyde type binders across a large range of products, including products in the building and automotive sector (e.g. mineral wool insulation, wood boards, particle boards, plywood, office panels, and acoustical sound insulation). In particular, previously developed formaldehyde-free binders may not possess all of the desired properties. For example, acrylic acid and poly(vinylalcohol) based binders have shown promising performance characteristics for some (but not all) products. However, these are relatively more expensive than phenol formaldehyde binders, are derived essentially from petroleum-based resources, and have a tendency to exhibit lower reaction rates compared to the phenol formaldehyde based binder compositions (requiring either prolonged cure times or increased cure temperatures).

Carbohydrate-based binder compositions are made of relatively inexpensive precursors and are derived mainly from renewable resources. However, these binders may also require reaction conditions for curing that are substantially different from those conditions under which the traditional phenol formaldehyde binder system is cured.

Specifically, a versatile alternative to the above-mentioned phenol formaldehyde binders is the use of carbohydrate polyamine binders which are polymeric binders obtained by reaction of carbohydrates with polyamines having at least one primary amine group. These carbohydrate polyamine binders are effective substitutes for phenol formaldehyde binders, since they possess similar or superior binding characteristics and are highly compatible to the established processes.

Typically, the carbohydrate polyamine binders are prepared as a solution, such as an aqueous solution, and are subsequently applied onto the loosely assembled matter to be bound. The such wetted loosely assembled matter is then, for example, heat treated to cure the carbohydrate polyamine binder.

Nonetheless, the rather high concentration of solids in the carbohydrate polyamine binder solution is connected to a variety of disadvantages, such as quick gelling or solidification of the binder solution, as well as recrystallization of the carbohydrate component. Based on the rather short shelf-life, further problems regarding storage and shipment of the carbohydrate polyamine binders are observed.

Accordingly, the technical problem underlying the present invention is to provide improved binders, particularly binders which are compatible with the established processes, are environmentally acceptable and overcome the aforementioned problems.

SUMMARY

In order to solve the above technical problem, as a first aspect, the present invention provides a water-soluble pre-reacted binder composition, comprising the reaction product(s) of (i) at least one carbohydrate component, and (ii) at least one nitrogen-containing component.

The pre-reacted binder may be in the form of an aqueous solution or dispersion containing at least 20 wt.-%, for example at least 25% wt.-, 30% wt.-, 35% wt.-, 40% wt.-, 45 wt.-%, 50 wt.-%, 55 wt.-%, 60 wt.-%, 65 wt.-%, 70 wt.-%, 75 wt.-% or 80 wt.-% of said pre-reacted binder composition and/or no more than 85 wt.-%, for example no more that 80 wt.-%, 75 wt.-% or 70 wt.-% of said pre-reacted binder composition.

DETAILED DESCRIPTION

Figure 1:
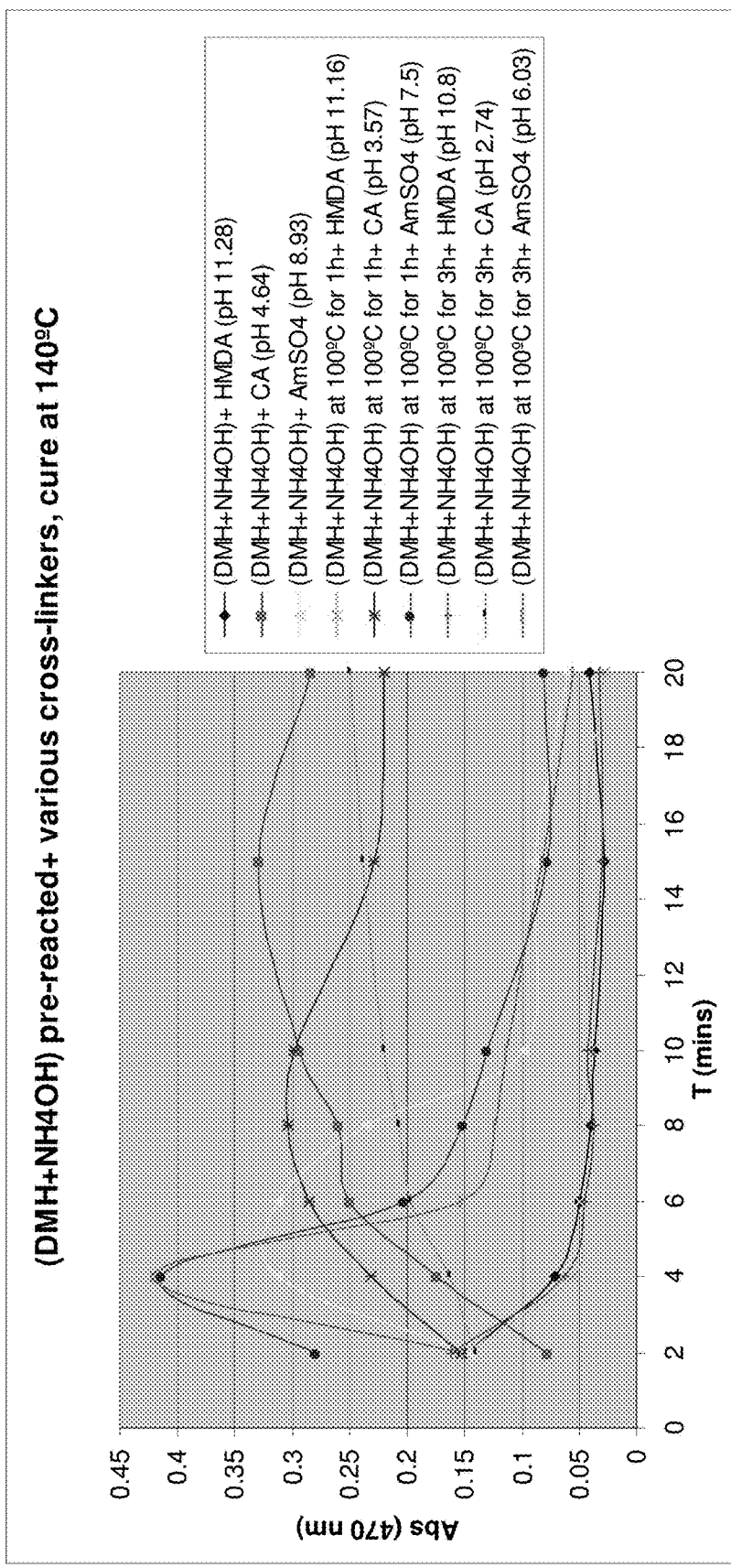
FIG. 1 shows: Cure rates of dextrose binders pre-reacted with ammonia and their pH.

According to the present invention, the term "pre-reacted binder composition" is not particularly restricted and generally includes any chemical composition obtainable and/or obtained by reacting a carbohydrate component and a nitrogen-containing component, which may be used as a binder, e.g. for binding loosely assembled matter, either as such or upon further modification.

The pre-reacted binder composition of preferred embodiments of present invention is based on a carbohydrate component/nitrogen-containing component binder system, i.e. the carbohydrate component(s) and nitrogen-containing component(s) are not only present in small amounts in the starting material to prepare the pre-reacted binder composition of the present invention, but are the major components of the starting material. Accordingly, the total amount of the at least one carbohydrate component and the at least one nitrogen-containing component in the starting material to prepare the pre-reacted binder composition may be at least 20 wt.-%, based on the total weight of the binder composition before pre-reaction. For example, the total amount of the at least one carbohydrate component and the at least one nitrogen-containing component may be at least 30 wt.-%, 40 wt.-%, 50 wt.-%, 60 wt.-%, 70 wt.-%, 80 wt.-%, 90 wt.-%, 95 wt.-%, or 98 wt.-% before pre-reaction.

According to one embodiment of the present invention, the total amount of the reaction product(s) of (i) at least one carbohydrate component and (ii) at least one nitrogen-containing component, the unreacted carbohydrate component(s) and the unreacted nitrogen-containing component(s) in the pre-reacted binder composition, i.e. (amount of reaction product(s) of (i) and (ii))+(amount of unreacted carbohydrate component(s))+(amount of unreacted nitrogen-containing component(s)), is at least 20 wt.-%, based on the total weight of the pre-reacted binder composition, for example at least 30 wt.-%, 40 wt.-%, 50 wt.-%, 60 wt.-%, 70 wt.-%, 80 wt.-%, 90 wt.-%, 95 wt.-%, or 98 wt.-%.

Compared with the state of the art where carbohydrate and polyamine reactants are dissolved to form a binder which is applied to loosely assembled matter and subsequently crosslinked by application of heat to yield a polymeric binder, the pre-reacted binder composition is a composition that: a) compared with such prior art binders as applied to loosely assembled matter (notably prior to crosslinking by application of heat) may have: intermediate reaction specie(s) such as pre-polymers, in significant quantities, and/or reduced viscosity per solid content and/or increased average molecular weight, and/or increased colour and/or light (eg UV) absorption; and/or b) compared with such prior art binders once partially or fully crosslinked (notably subsequent to application of heat) may have a significantly lower degree and/or or a different kind of crosslinkage and/or lower viscosity.

As used herein, the term "pre-polymer" is not specifically restricted and includes any reaction product(s) of (i) the at least one carbohydrate component and (ii) the at least one nitrogen-containing component.

According to one embodiment of the present invention, the amount of the reaction product(s) of (i) at least one carbohydrate component and (ii) at least one nitrogen-containing component is at least 20 wt.-%, based on the total weight of pre-polymers in the pre-reacted binder composition, for example at least 30 wt.-%, 40 wt.-%, 50 wt.-%, 60 wt.-%, 70 wt.-%, 80 wt.-%, 90 wt.-%, 95 wt.-%, or 98 wt.-%. According to a specific embodiment, the amount of the reaction product(s) of (i) at least one carbohydrate component and (ii) at least one nitrogen-containing component is 100 wt.-%, based on the total weight of pre-polymers in the pre-reacted binder composition.

According to one embodiment, the pre-reacted binder composition of the present invention comprises at least one pre-polymer having a molecular weight in the range of 1 to 500 kDa. Preferably, said at least one pre-polymer is contained, based on the total weight of the binder composition, in an amount of 2 wt.-% or more, e.g. 5 wt.-% or more, 10 wt.-% or more, 15 wt.-% or more, 20 wt.-% or more, 25 wt.-% or more, 30 wt.-% or more, 35 wt.-% or more, 40 wt.-% or more, 45 wt.-% or more, or 50 wt.-% or more.

According to a further embodiment, the pre-reacted binder composition of the present invention comprises at least one pre-polymer having a molecular weight in the range of more than 80 to 500 kDa (high molecular-weight pre-polymer). Preferably, said at least one high molecular-weight pre-polymer is contained, based on the total weight of the binder composition, in an amount of 0.2 wt.-% or more, e.g. 0.5 wt.-% or more, 0.75 wt.-% or more, 1 wt.-% or more, 1.75 wt.-% or more, 2.5 wt.-% or more, 5 wt.-% or more, 10 wt.-% or more, 15 wt.-% or more, 20 wt.-% or more, 30 wt.-% or more, 40 wt.-% or more, or 50 wt.-% or more.

According to a further embodiment, the pre-reacted binder composition of the present invention comprises at least one pre-polymer having a molecular weight in the range of more than 10 to 80 kDa (mid molecular-weight pre-polymer). Preferably, said at least one mid molecular-weight pre-polymer is contained, based on the total weight of the binder composition, in an amount of 0.3 wt.-% or more, e.g. 0.5 wt.-% or more, 1 wt.-% or more, 1.5 wt.-% or more, 2 wt.-% or more, 2.5 wt.-% or more, 5 wt.-% or more, 10 wt.-% or more, 15 wt.-% or more, 20 wt.-% or more, 30 wt.-% or more, 40 wt.-% or more, or 50 wt.-% or more.

According to a further embodiment, the pre-reacted binder composition of the present invention comprises one or more compounds having a molecular weight in the range of 10 kDa or less (low molecular-weight pre-polymer), and which are different from (i) the at least one carbohydrate component and (ii) the at least one nitrogen-containing component. According to a specific embodiment, the low molecular-weight compounds comprise one or more of a glycolaldehyde, glyceraldehyde, 2-oxopropanal, acetol, dihydroxyacetone, acetoin, butanedione, ethanal, glucosone, 1-desoxyhexosulose, 3-desoxyhexosulose, 3-desoxypentosulose, 1,4-didesoxyhexosulose, glyoxal, methylglyoxal, diacetyl and 5-(hydroxymethyl)furfural.

Moreover, herein the term "water-soluble" is not specifically restricted and includes all grades of water-solubility of the pre-reacted binder composition as defined above. In particular, the term "water-soluble" includes water-solubility at 20° C. of 100 g/l or more, 150 g/l or more, 200 g/l or more, or 250 g/l or more. For example, the term "water-soluble" may include a water-solubility of the pre-reacted binder composition as defined above of 300 g/l or more, 400 g/l or more, 500 g/l or more or 600 g/l or more (at 20° C.). Also virtual infinite water-solubility may be regarded to be within the scope of the present invention.

In this context, the expression "water-insoluble" according to the present invention relates to cases where the pre-reacted binder composition as defined above is essentially not soluble in water at 20° C. For example, the term insoluble includes a water-solubility at 20° C. of 50 g/l or less, 40 g/l or less, 30 g/l or less, or 20 g/l or less. Preferably, the term water-insoluble includes cases of water-solubility of 10 g/l or less, 5 g/l or less, 1 g/l or less or 0.1 g/l or less.

The pre-reacted binder composition may be water dilutable where this means that 1 part by weight of pre-reacted binder composition mixed with at least 25 parts, notably at least 50 parts or 100 parts of deionized water does not form a precipitation upon mixing.

According to a preferred embodiment of the present invention, an aqueous solution containing 70 wt.-% of the pre-reacted binder composition of the present invention has a viscosity at 20° C. of at most 2000 cP. For example, an aqueous solution containing 70 wt.-% of the above-defined the prereacted binder composition (i.e. an aqueous solution containing 70% wt.-% of solids) may have an initial viscosity after its preparation of 100 to 1500 cP, of 150 to 1200 cP, of 200 to 800 cP, of 220 to 600 cP, or of 250 to 400 cP. From the viewpoint of handling, a preferred viscosity is in the range of 280 to 350 cP. Viscosity may be measured using a LV-Torque Brookfield Viscometer, spindle LV-63 at 60 rpm.

Moreover, the viscosity of said aqueous solution should preferably not increase by more than 500 cP when left to stand at 20° C. for 12 hours, 24 hours, 48 hours, 72 hours or 96 hours. According to a further preferred embodiment, the viscosity of said aqueous solution should not increase by more than 500 cP within a week, 10 days, 12 days or two weeks. Longer periods, such as three or four weeks, or even two, three or more months, where the viscosity will not increase by more than 500 cP are even more preferable.

According to a further embodiment, the amount by which the viscosity increases within the first 12 hours when leaving an 70 wt.-% aqueous solution of the pre-reacted binder composition to stand at 20° C. should preferably not exceed 450 cP, or 400 cP or even 350 cP. Preferred increases in viscosity include increases of 300 cP or less, 280 cP or less, 250 cP or less and 200 cP or less.

According to the present invention, the above-defined time periods and increases in viscosity are not limited to the examples mentioned above and may be freely combined. For example, preferably, the above-mentioned 70 wt.-% aqueous solution of the pre-reacted binder composition does not increase in viscosity by more than 300 cP within the first 48 hours after its preparation, or more than 400 cP within two weeks after its preparation. Generally, if the viscosity of a respective aqueous solution becomes too high, e.g. caused by gelling, the pre-reacted binder composition may become unusable.

According to a further embodiment, the above-defined pre-reacted binder composition is capable of reacting with a crosslinker to yield a water-insoluble composition, for example to yield one or more melanoidins as a water-insoluble composition. In the present invention, the pre-reacted binder composition may function as a precursor or intermediate which may be further reacted with a crosslinker to obtain a polymeric binder. For example, this polymeric binder may contain high molecular weight melanoidins as Maillard reaction products which are essentially water-insoluble.

For example, the one or more melanoidins as defined above may contain the following generic structural motifs:

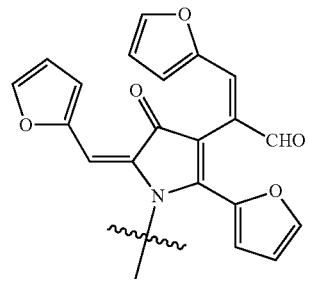

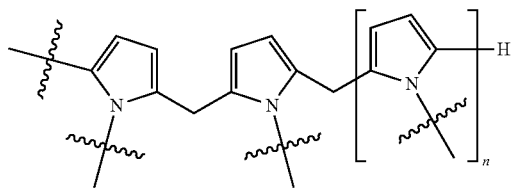

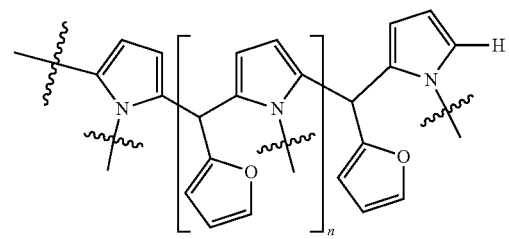

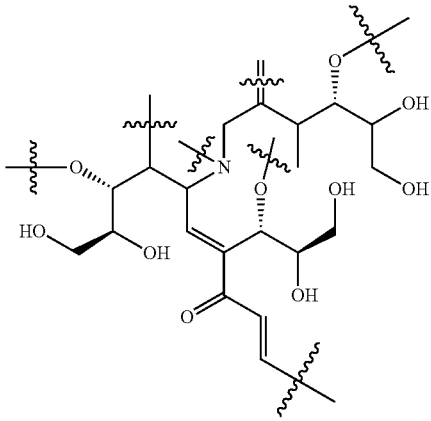

wherein n is an integer of at least 1.

Herein, the term "crosslinker" is not particularly restricted and includes any chemical or physical means to further crosslink the pre-reacted binder composition to yield a polymeric binder suitable for binding loosely assembled matter, such as wood or mineral fibers.

According to a specific embodiment of the present invention, the crosslinker may be the same nitrogen-containing component which has been reacted with the carbohydrate component, or may be a different nitrogen-containing component. For example, the pre-reacted binder composition of the present invention may be prepared by reacting a carbohydrate component with hexamethylenediamine. Subsequently, further hexamethylenediamine may be added to the pre-reacted binder composition to achieve the high grade of polymerization required in the respective application. A further example includes the case where the pre-reacted binder composition is prepared by reacting a carbohydrate component with an aqueous solution of ammonia, and for the final curing additional hexamethylenediamine is added.

However, according to the present invention, the crosslinker is not limited to the nitrogen-containing components defined herein and includes, as an example, Lewis acids, isocyanates, blocked isocyanates, epoxides, blocked epoxides, carbonyl-containing compounds (aldehydes, ketones, i.e. glyoxal) and organic carbonates. Specific examples of the crosslinker include citric acid, polycarboxylic acids and anhydrides (e.g. succinic acid, maleic anhydride, tetra- and hexahydrophthalic anhydrides, styrene-maleic-anhydride copolymers), solutions of polycarboxylic acid and anhydride derivatives (e.g. ammonium salts thereof).

According to a further embodiment of the above-defined pre-reacted binder composition, the ratio of the total carbonyl groups in the carbohydrate component to total reactive nitrogen-containing groups in the nitrogen-containing component is 5:1 to 1:5. For example, the ratio of carbonyl groups to reactive nitrogen-containing groups may be 5:1 to 1:4.5, 5:1 to 1:4, 5:1 to 1:3.5, 5:1 to 1:3, 5:1 to 1:2.5, 5:1 to 1:2, 5:1 to 1:1.8, 5:1 to 1:1.5, 5:1 to 1:1.2, 5:1 to 1:1, 5:1 to 1:0.8 and 5:1 to 1:0.5. Further examples include ratios such as 4:1 to 1:5, 3.5:1 to 1:5, 3:1 to 1:5, 2.5:1 to 1:5, 2:1 to 1:5, 1.5:1 to 1:5, 1:1 to 1:5, 0.8:1 to 1:5 and 0.5:1 to 1:5. According to the present invention, the upper and lower borders of the above-mentioned ratios may be freely combined.

Herein, the term "reactive nitrogen-containing group" is not particularly restricted and includes any nitrogen-containing groups in the nitrogen-containing component which are capable of reacting with the carbohydrate component. Specifically, examples of such reactive nitrogen-containing groups include primary, secondary, tertiary and quaternary amine groups, amide groups, imine and imide groups, as well as cyanate and isocyanate groups.

Herein, the term "carbohydrate component" is not specifically restricted and generally includes any carbohydrate compound which is capable of reacting with a nitrogen-containing component.

According to one embodiment of the above-defined pre-reacted binder, the at least one carbohydrate component is selected from the group consisting of monosaccharides, disaccharides, polysaccharides or a reaction product thereof.

Preferably, the carbohydrate component is or comprises a reducing sugar and/or a component which yields a reducing sugar in situ. As used herein, the term "reducing sugar" indicates one or more sugars that contain aldehyde or keto-groups, or that can isomerize, i.e., tautomerize, to contain aldehyde or keto-groups, which groups may be oxidized with, for example, Cu-ions to afford carboxylic acids. According to the present invention, any such carbohydrate component may be optionally substituted, such as with hydroxy, halo, alkyl, alkoxy, and the like. In any such carbohydrate component, one or more chiral centers may be present, and both possible optical isomers at each chiral center are included in the invention described herein. Further, it is also to be understood that various mixtures, including racemic mixtures, or other diastereomeric mixtures of the various optical isomers of any such carbohydrate component, as well as various geometric isomers thereof, may be used in one or more embodiments described herein.

Non-reducing sugars, for instance sucrose, may be used as the or part of the carbohydrate component, especially when capable and/or subjected to in-situ conversion to a reducing sugar. Further, it is also understood that a monosaccharide, a disaccharide, or a polysaccharide may be partially reacted with a precursor to form a carbohydrate reaction product. To the extent that the carbohydrate reaction product is derived from a monosaccharide, a disaccharide, or a polysaccharide, and maintains similar reactivity with the nitrogen-containing component to form reaction products similar to those of a monosaccharide, a disaccharide, or a polysaccharide with a nitrogen-containing component, the carbohydrate reaction product is within the scope of term carbohydrate component.

Preferably, any carbohydrate component should be sufficiently nonvolatile to maximize its ability to remain available for reaction with the nitrogen-containing component. The carbohydrate component may be a monosaccharide in its aldose or ketose form, including a triose, a tetrose, a pentose, a hexose, or a heptose; or a polysaccharide; or combinations thereof. For example, when a triose serves as the carbohydrate component, or is used in combination with other reducing sugars and/or a polysaccharide, an aldotriose sugar or a ketotriose sugar may be utilized, such as glyceraldehyde and dihydroxyacetone, respectively. When a tetrose serves as the carbohydrate component, or is used in combination with other reducing sugars and/or a polysaccharide, aldotetrose sugars, such as erythrose and threose; and ketotetrose sugars, such as erythrulose, may be utilized. When a pentose serves as the carbohydrate component, or is used in combination with other reducing sugars and/or a polysaccharide, aldopentose sugars, such as ribose, arabinose, xylose, and lyxose; and ketopentose sugars, such as ribulose, arabulose, xylulose, and lyxulose, may be utilized. When a hexose serves as the carbohydrate component, or is used in combination with other reducing sugars and/or a polysaccharide, aldohexose sugars, such as glucose (i.e., dextrose), mannose, galactose, allose, altrose, talose, gulose, and idose; and ketohexose sugars, such as fructose, psicose, sorbose and tagatose, may be utilized. When a heptose serves as the carbohydrate component, or is used in combination with other reducing sugars and/or a polysaccharide, a ketoheptose sugar such as sedoheptulose may be utilized. Other stereoisomers of such carbohydrate components not known to occur naturally are also contemplated to be useful in preparing the binder compositions as described herein. In one embodiment, the carbohydrate component is high fructose corn syrup (HFCS).

As mentioned above, the carbohydrate component may be polysaccharide. For example, the carbohydrate component may be polysaccharide with a low degree of polymerization and includes e.g. molasses, starch, cellulose hydrolysates, or mixtures thereof. According to a specific example, the carbohydrate component is a starch hydrolysate, a maltodextrin, or a mixture thereof. While carbohydrates of higher degrees of polymerization may not be preferable, they may none the less be useful within the scope of the present invention by in-situ depolymerization.

Furthermore, according to the present invention, the carbohydrate component may be used in combination with a non-carbohydrate polyhydroxy reactant. Examples of non-carbohydrate polyhydroxy reactants which can be used in combination with the carbohydrate component include, but are not limited to, trimethylolpropane, glycerol, pentaerythritol, polyvinyl alcohol, partially hydrolyzed polyvinyl acetate, fully hydrolyzed polyvinyl acetate, and mixtures thereof. For example, the non-carbohydrate polyhydroxy reactant is sufficiently nonvolatile to maximize its ability to remain available for reaction with a monomeric or polymeric polyamine. Moreover, according to the present invention, the hydrophobicity of the non-carbohydrate polyhydroxy reactant may be a factor in determining the physical properties of a binder prepared as described herein. Other co-reacting compounds, for example, like carbonyl-containing compounds—aldehydes, ketones, carboxylic acids and anhydrides, may be used.

In a preferred embodiment of the above-defined pre-reacted binder composition, the at least one carbohydrate component is selected from the group consisting of ribose, arabinose, xylose, lyxose, glucose (dextrose), mannose, galactose, allose, altrose, talose, gulose, idose, fructose, psicose, sorbose, dihydroxyacetone, sucrose and tagatose, as well as mixtures thereof.

Further, herein the expression "nitrogen-containing component" is not particularly limited and includes any chemical compound, or mixture of compounds, which contain at least one nitrogen atom and which is capable of reacting with the at least one carbohydrate component.

According to one embodiment, in the pre-reacted binder composition as defined above, the at least one nitrogen-containing component is $NH_3$, an inorganic amine or an organic amine comprising at least one primary amine group, as well as salts thereof. For example, as the nitrogen-containing component $NH_3$ may be used as such (e.g. in form of an aqueous solution), as well as any type of inorganic and organic ammonium salts, as long as these salts are capable of reacting with the carbohydrate component defined above. Specific examples of inorganic ammonium salts include ammonium sulfate ($AmSO_4$), ammonium phosphate, ammonium chloride, and ammonium nitrate.

According to the present invention, the nitrogen-containing component may be a polyamine. Herein, the term "polyamine" includes any organic compound having two or more amine groups, which may independently be substituted. As used herein, a "primary polyamine" is an organic compound having two or more primary amine groups ($—NH_2$). Within the scope of the term primary polyamine are those compounds which can be modified in situ or isomerize to generate a compound having two or more primary amine groups ($—NH_2$).

For example, the polyamine may be a primary polyamine. According to one embodiment of the present invention, the primary polyamine may be a molecule having the formula $H_2N$-Q-$NH_2$, wherein Q is an alkyl, cycloalkyl, heteroalkyl, or cycloheteroalkyl, each of which may be optionally substituted. For example, Q may be an alkyl group selected from a group consisting of $C_2$-$C_{24}$, an alkyl selected from a group consisting of $C_2$-$C_9$, an alkyl selected from a group consisting of $C_3$-$C_7$. According to a preferred embodiment, Q is a $C_6$ alkyl. According to another embodiment, Q may be a cyclohexyl, cyclopentyl or cyclobutyl, or a benzyl group.

As used herein, the term "alkyl" includes a chain of carbon atoms, which may optionally be branched. As used herein, the terms "alkenyl" and "alkynyl" independently include a chain of carbon atoms, which may optionally be branched, and include at least one double bond or triple bond, respectively. It is to be understood that alkynyl may also include one or more double bonds. It is to be further understood that alkyl is advantageously of limited length, including $C_1$-$C_{24}$, $C_1$-$C_{12}$, $C_1$-$C_8$, $C_1$-$C_6$, and $C_1$-$C_4$. It is to be further understood that alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. In particular, shorter alkyl, alkenyl, and/or alkynyl groups may add less hydrophilicity to the compound and accordingly will have different reactivity towards the carbohydrate component and solubility in a binder solution.

As used herein, the term "cycloalkyl" includes a chain of carbon atoms, which may optionally be branched, where at least a portion of the chain is cyclic. Moreover, according to the present invention it is to be noted that the term "cycloalkylalkyl" is regarded as a subset of cycloalkyl, and that the term "cycloalkyl" also includes polycyclic structures. For example, such cycloalkyls include, but are not limited to, cyclopropyl, cyclopentyl, cyclohexyl, 2-methyl-cyclopropyl, cyclopentyleth-2-yl, adamantyl, and the like. As used herein, the term "cycloalkenyl" includes a chain of carbon atoms, which may optionally be branched, and includes at least one double bond, where at least a portion of the chain is cyclic. According to the present invention, said at least one double bond may be in the cyclic portion of cycloalkenyl and/or the non-cyclic portion of cycloalkenyl. Moreover, it is to be understood that cycloalkenylalkyl and cycloalkylalkenyl are each regarded as subsets of cycloalkenyl. Moreover, according to the present invention "cycloalkyl" may be polycyclic. Examples of such cycloalkenyls include, but are not limited to, cyclopentenyl, cyclohexylethen-2-yl, cycloheptenylpropenyl, and the like. Furthermore, the chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. According to the present invention, shorter alkyl and/or alkenyl chains forming cycloalkyl and/or cycloalkenyl, respectively, may add less lipophilicity to the compound and accordingly will have different behavior.

As used herein, the term "heteroalkyl" includes a chain of atoms that includes both carbon and at least one heteroatom, and is optionally branched. Examples of such heteroatoms include nitrogen, oxygen, and sulfur. In certain variations, said hetero-atoms also include phosphorus, and selenium. In one embodiment, a heteroalkyl is a polyether. As used herein, the term "cycloheteroalkyl" including heterocyclyl and heterocycle, includes a chain of atoms that includes both carbon and at least one heteroatom, such as heteroalkyl, and may optionally be branched, where at least a portion of the chain is cyclic. Similarly, examples of cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

Herein, the term "optionally substituted" includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

For example, the primary polyamine may be a diamine, triamine, tetraamine, or pentamine. According to one embodiment, the polyamine is a triamine selected from a diethylenetriamine, 1-piperazineethaneamine, or bis(hexamethylene)triamine. In another embodiment, the polyamine is a tetramine, for example triethylenetetramine. In another embodiment, the polyamine is a pentamine, for example tetraethylenepentamine.

One aspect of the primary polyamine is that it may possess low steric hindrance. For example, 1,2-diaminoethane, 1,4-diaminobutane, 1,5-diaminopentane, 1,6-diaminohexane, 1,12-diaminododecane, 1,4-diaminocyclohexane, 1,4-diaminoben-zene, diethylenetriamine, triethylenetetramine, tetraethylenepentamine, 1-piperazine-ethaneamine, 2-methyl-pentamethylenediamine, 1,3-pentanediamine, and bis(hexamethylene)triamine, as well as 1,8-diaminooctane have low steric hindrance within the scope of the present invention. According to a preferred embodiment of the pre-reacted binder composition as defined above, the nitrogen-containing component is the primary polyamine 1,6-diaminohexane (hexamethylenediamine, HMDA). In a further embodiment the nitrogen-containing component is 1,5-diamino-2-methylpentane (2-methyl-pentamethylenediamine). In another embodiment, the nitrogen-containing component is the primary polyamine polyether-polyamine. For example, according to the present invention, said polyether-polyamine is a diamine or a triamine. In one embodiment, the polyether-polyamine is a trifunctional primary amine having an average molecular weight of 440 known as Jeffamine T-403 Polyetheramine (Huntsman Corporation). EDR-104 and EDR-148 (Huntsman) may also be used.

In a further embodiment, the nitrogen-containing component may include a polymeric polyamine. For example, polymeric polyamines within the scope of the present invention include chitosan, polylysine, polyethylenimine, poly(N-vinyl-N-methyl amine), polyaminostyrene and polyvinylamines. In a specific example, the nitrogen-containing component comprises a polyvinyl amine. As used herein, the polyvinyl amine can be a homopolymer or a copolymer.

The term "solvent" used herein is not particularly restricted and includes any solvent which may be used to carry out a reaction between the carbohydrate component and the nitrogen-containing component. For example, the solvent may be water, an organic solvent or mixtures thereof. Examples of organic solvents include alcohols, ethers, esters, ketones, aldehydes, alkanes and cycloalkanes. Preferably, the solvent consists of or consists essentially of water.

According to a further embodiment, the above-defined pre-reacted binder composition has an average molecular weight in the range of 200 to 5000 g/mol. According to the present invention, the average molecular weight of the pre-reacted binder composition may range from 300 to 4500 g/mol, from 400 to 4000 g/mol, from 450 to 3500 g/mol, from 500 to 300 g/mol or from 600 to 1500 g/mol. However, the average molecular weight of the pre-reacted binder composition is not limited to said ranges and the upper and lower values thereof may be freely combined.

A further embodiment of the present invention relates to the above-defined pre-reacted binder composition, wherein the weight ratio between the carbohydrate component and the nitrogen-containing component is 0.5:1 to 30:1. Examples of further molar ratios include ratios of 0.7:1 to 25:1, 1:1 to 22:1, 1.5:1 to 20:1, 2:1 to 15:1, 2.5:1 to 10:1 or 3:1 to 8:1. However, according to the present invention, the molar ratio of carbohydrate component to nitrogen-containing component is not limited to said ranges and the above upper and lower borders may be freely combined.

A further embodiment relates to the pre-reacted binder composition as defined above comprising at least 10% of the initial carbonyl groups provided by the carbohydrate component. In particular, in some embodiments of the pre-reacted binder composition of the present invention some of the initial carbonyl groups of the carbohydrate component have not reacted with the nitrogen-containing component and are still present therein. Further examples of the number of unreacted carbonyl groups in the pre-reacted binder composition include at least 15%, at least 20%, at least 25%, at least 30%, at least 35%, at least 40%, at least 50%, at least 60% or at least 75% of the carbonyl groups present in the carbohydrate component before reaction with the nitrogen-containing component. According to a specific embodiment, the initial carbonyl groups are present in the form of unreacted carbohydrate.

As used herein, the expression "unreacted carbohydrate" component relates to any compound of the (i) at least one carbohydrate component which is still present in its initial form, i.e. which has not undergone any reaction. According to one embodiment, the pre-reacted binder composition comprises, based on the total weight of the binder composition, up to 80 wt.-% of unreacted carbohydrate, e.g. up to 75 wt.-%, up to 70 wt.-%, up to 65 wt.-%, up to 60 wt.-%, up to 55 wt.-% or up to 50 wt.-%.

Depending on its chemical composition, the pre-reacted binder composition of the present invention may be used as such, i.e. by applying it to loosely assembled matter and curing it, for example through application of heat and/or radiation to arrive at a polymeric binder.

In a further embodiment, the pre-reacted binder composition may be used by subsequently adding a crosslinker, applying the mixture onto the loosely assembled matter and curing the mixture, thus forming a highly crosslinked polymeric binder having similar or even improved properties over the known carbohydrate-based binders. In this case, the pre-reacted binder composition of the present application may advantageously be prepared, stored and/or shipped, and used later and/or at a different place by adding a crosslinker, to complete the final binder composition.

If not stated otherwise, any of the above definitions also apply to the further aspects and embodiments of the present invention described below.

A further aspect of the present invention relates to a method of manufacturing the pre-reacted binder composition as defined above, comprising the steps:
(i) providing at least one carbohydrate component,
(ii) providing at least one nitrogen-containing component,
(iii) mixing in a solvent the carbohydrate component(s) and the nitrogen-containing component(s), and
(iv) reacting the carbohydrate component(s) and nitrogen-containing component(s) in the solution or dispersion obtained in step (iii).

According to the present invention, the method of manufacturing the pre-reacted binder composition may be carried out under the same conditions (i.e. components and ratios) as defined above in respect to the pre-reacted binder composition.

In a preferred embodiment, the preparation of the pre-reacted binder composition is carried out in a solvent, such as water, to directly yield a binder solution usable for storage, shipping or as a basis for preparing the final binder composition. For example, the pre-reacted binder composition may be prepared in a concentrated aqueous solution of the carbohydrate component and nitrogen-containing component. The thus obtained concentrated pre-reacted binder solution may then be used, for example, at a later time and/or a different place, e.g. by dilution and addition of a cross-linker, as an effective binder for consolidating loosely assembled matter.

According to a preferred embodiment of the present invention, the above steps (i) to (iv) are carried out while the carbohydrate component(s) and nitrogen-containing component(s) are not in contact with a collection of matter which is to be bound by a polymeric binder.

The temperature in step (iv) of the above method of manufacturing the pre-reacted binder composition of the present invention is not specifically restricted and includes temperatures in the range of 10 to 120° C., 15 to 110° C., 20 to 100° C. or 25 to 90° C. For example, the reaction temperature may range from 25 to 85° C., 30 to 80° C., 35 to 75° C. or 40 to 70° C. Specific examples of the temperature range include 40 to 90° C., 45 to 85° C. and 50 to 75° C. According to the present invention, the temperature at which the pre-reacted binder composition is prepared is not limited to the above ranges, and the upper and lower values of said ranges may be freely combined.

According to one embodiment, reaction step (iv) of the above method is carried out by reacting the carbohydrate component(s) and nitrogen-containing component(s) at a temperature of at most 120° C., e.g. of at most 115° C., at most 110° C., at most 105° C., at most 100° C., at most 95° C., at most 90° C., at most 85° C. or at most 80° C.

Similarly, the duration of reacting the carbohydrate component(s) and nitrogen-containing component(s) in reaction step (iv) in the above method is not specifically restricted and includes durations of 5 to 240 minutes, 5 to 210 minutes, 5 to 180 minutes, 5 to 150 minutes, 5 to 120 minutes, 5 to 90 minutes, 5 to 75 minutes 5 to 60 minutes, 5 to 40 minutes, 5 to 30 minutes and 5 to 25 minutes. Further examples include durations of 5 to 240 minutes, 10 to 240 minutes, 15 to 240 minutes, 20 to 240 minutes, 25 to 240 minutes, 30 to 240 minutes, 40 to 240 minutes, 45 to 240 minutes, 60 to 240 minutes, 120 to 240 minutes and 180 to 240 minutes. However, durations of up to one, two, three, four, five and six days, as well as durations of one, two or three weeks may also be reasonable within the scope of the present invention. According to the present invention, the duration for preparing the pre-reacted binder composition as defined above is not limited to the above examples and the upper and lower values of said ranges may be freely combined herein.

According to one embodiment, reaction step (iv) is carried out by reacting the carbohydrate component(s) and nitrogen-containing components for a period of at most 96 hours, e.g. of at most 90 hours, at most 85 hours, at most 80 hours, at most 75 hours, at most 70 hours, at most 65 hours, at most 60 hours, at most 55 hours, at most 50 hours, at most 45 hours, at most 40 hours, at most 35 hours, at most 30 hours, at most 25 hours, at most 20 hours, at most 15 hours, at most 10 hours, at most 5 hours or at most 3 hours. Reaction step (iv) may be carried out by reacting the carbohydrate component(s) and nitrogen-containing component(s) for a period of at least 5, 10, 15, 20, 25, 30, 40, 60 12 or 180 minutes.

According to a specific embodiment, reaction step (iv) is carried out by reacting the carbohydrate component(s) and nitrogen-containing component(s) at a temperature range of 40 to 120° C. for a period of 5 to 180 minutes.

According to another specific embodiment, reaction step (iv) is carried out by reacting the carbohydrate component(s) and nitrogen-containing component(s) at a temperature range of 20 to 30° C. for a period of 1 to 96 hours.

According to the present invention, the duration and temperature for carrying out reaction step (iv) in the above method is not limited to the above examples and the upper and lower values of said ranges may be freely combined herein.

According to a further embodiment, the viscosity of the solution or dispersion during step (iv) of reacting the carbohydrate component(s) and the nitrogen-containing component(s) does not increase by more than 300 cP, when determined at 20° C. and a starting concentration of 70 wt.-% total carbohydrate and nitrogen-containing components present before said step (iv). For example, the viscosity does not increase by more than 275 cP, more than 250 cP, more than 225 cP, more than 200 cP, more than 175 cP, more than 150 cP, more than 100 cP, more than 75 cP, or more than 50 cP.

The reaction step (iv) may be carried out at or substantially at atmospheric pressure, for example in an open reaction vessel. Alternatively, the reaction step (iv) may be carried out in a closed reaction vessel; it may be carried out at a pressure above atmospheric pressure.

According to another aspect, the present invention relates to a water-soluble pre-reacted binder composition obtainable by the method as defined above.

For example, one embodiment relates to the pre-reacted binder composition as defined above, wherein said binder-composition is obtainable by reacting in a solvent the at least one carbohydrate component with the at least one nitrogen-containing component at a temperature of at least 10° C. for a period of at least 5 minutes.

According to another aspect, the present invention relates to a use of the water-soluble pre-reacted binder composition as defined above in the manufacture of a product comprising a collection of matter bound by a polymeric binder.

Herein, the term "collection of matter" is not particularly restricted and includes any collection of matter which comprises fibers selected from the group consisting of mineral fibers (including slag wool fibers, stone wool fibers, glass fibers), aramid fibers, ceramic fibers, metal fibers, carbon fibers, polyimide fibers, polyester fibers, rayon fibers, and cellulosic fibers. Further examples of a collection of matter include: particulates such as coal, sand; cellulosic fibers; wood shavings, sawdust, wood pulp, ground wood, wood chips, wood strands, wood layers; other natural fibers such as jute, flax, hemp, and straw; wood veneers; facings; wood facings, particles, woven or non-woven materials (e.g. comprising fibers, notably of the type(s) referred to above).

A further aspect of the present invention relates to a method of manufacturing a collection of matter bound by a polymeric binder comprising the steps:
(i) providing a collection of matter,
(ii) providing the above-defined pre-reacted binder composition, or a pre-reacted binder composition obtained by the method as defined above, in a solvent to obtain a solution or dispersion,
(iii) applying the solution or dispersion obtained in step (ii) to the collection of matter, and
(iv) applying energy to the collection of matter containing said solution or dispersion to cure the binder composition.

The step (iv) of applying energy to the collection of matter as defined in the above method is not particularly restricted and includes, for example, heating in an oven at a temperature of 100° C. to 350° C., depending on the type of matter, the amount of binder and other conditions.

According to one embodiment of the above method, in step (ii) a crosslinker is added to the prereacted binder composition as defined above or the pre-reacted binder composition obtained by the method as defined above, or the solution or dispersion thereof.

In a further embodiment of the above-defined method of manufacturing a collection of matter, the pre-reacted binder composition as defined above or the pre-reacted binder composition obtained by the method as defined above has been aged for at least 24 hours before the cross-linker is added in step (ii). Further examples include ageing periods of at least 48 hours, at least 72 hours, at least 96 hours, at least one, two or three weeks, or at least one or two months.

According to the present invention, the pre-reacted binder composition may change over time in its chemical composition by continuing the reaction between the carbohydrate component and the nitrogen-containing component. For example, even at relatively low temperatures, such as room temperature (20° C.) or below, Maillard-type reactions may continue between the carbohydrate component and the nitrogen-containing component towards the formation of melanoidins. As a consequence, ageing of the pre-reacted binder composition may lead to an accelerated final curing process of the binder and/or to an improved bond strength.

According to a further embodiment of the above-defined method of manufacturing a collection of matter, prior to the step of applying the solution or dispersion obtained in step (ii) to the collection of matter, the collection of matter is substantially free of binder.

A further aspect of the present invention relates to a binder solution or dispersion comprising in a solvent the pre-reacted binder composition as defined above and a cross-linker.

The pre-reacted binder composition solution or dispersion, particularly in the state applied to the material to be bound, may comprise:
at least 5% 10%, 15% or 18% solids and/or
less than 80%, 70% or 60% (particularly in the case of wood board applications) or less than 50%, 40% or 20% solids (particularly in the case of mineral fibre insulation applications)
particularly determined as bake out solids by weight after drying at 140° C. for 2 hours.

According to a further aspect, the present invention relates to a fiber or particle-containing product comprising one or more types of fibers and/or particles and the pre-reacted binder composition as defined above in a cured state.

Binders in accordance with the present invention may be used as binders e.g. in articles selected from the group consisting of: thermal insulation materials; mineral wool insulation (including glass wool insulation and stone wool insulation); wood boards; fibreboards; wood particle boards; chip boards; orientated strand board; medium density fibreboards; plywood; high pressure laminates.

The quantity of binder in the finished product, particularly in the case of mineral wool insulation, may be:
Greater than: 1%, 2%, 2.5%, 3%, 3.5% or 4%; and/or
Less than: 20%, 15%, 10% or 8%
measured by dry weight of the finished product.

The quantity of binder for mineral wool insulation is typically measured by loss on ignition (LOI).

Particularly in the case of mineral fibre insulation, the products may have one or more of the following parting strengths:
Ordinary Parting Strength of
At least 120 g/g, preferably at least 150 g/g; and/or
Less than 400 g/g
Weathered Parting Strength of
At least 120 g/g, preferably at least 150 g/g; and/or
Less than 400 g/g
% loss between Ordinary and Weathered Parting Strength of
Less than 10%, preferably less than 5%

The parting strength is expressed in grams/gram being the total breaking load of six test specimens divided by their total weight. The test is carried out on mineral fibre mats as received for testing (Ordinary Parting Strength) and after an accelerated weathering test as explained below (Weathered Parting Strength).

Figure 14:
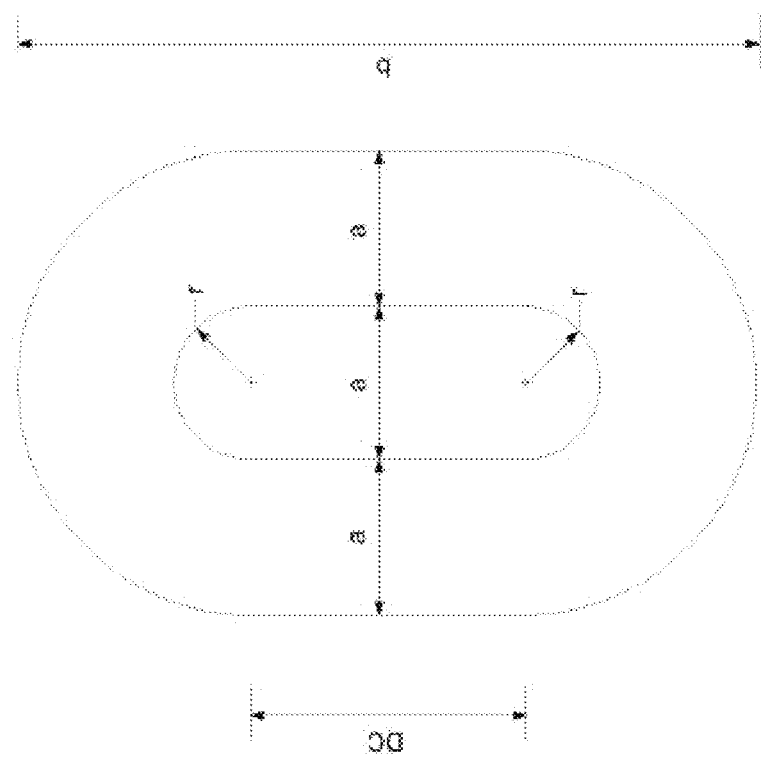
FIG. 14 shows: a plan view of a mineral fibre test sample.

A first set of six samples of the form and dimensions shown in FIG. 14 are cut from the mineral fibre mat to be tested. The dimensions are:
r: radius 12.7 mm;
DC: distance between centres 44.5 mm;
a: 25.4 mm;
b: 121 mm.

The long axis of the samples should be parallel to the conveyor direction and the samples should be taken across the full width of the mineral mat. A second set of six samples is then taken in the same way.

The total weight of the first group of six samples W1 in grams is recorded.

The total weight of the second group of six samples W2 in grams is recorded; these samples are then placed in a preheated autoclave and conditioned on a wire mesh shelf away from the bottom of the chamber under wet steam at 35 $kN/m^2$ for one hour. They are then removed, dried in an oven at 100° C. for five minutes and tested immediately for parting strength.

To test the parting strength, each sample is mounted in turn on the jaws of a 5500 Instron tensile strength machine and the maximum breaking load in grams or Newtons is recorded. If the breaking load is measured in Newtons it is converted to grams by multiplying it by 101.9. Six results in grams are obtained for each set of samples: G1 G2 G3 G4 G5 and G6 for the first set of samples and G7 G8 G9 G10 G11 and G12 for the second set of samples.

The Ordinary Parting Strength is calculated from the first set of samples using the formula Ordinary Parting Strength=(G1+G2+G3+G4+G5+G6)/W1.

The Weathered Parting Strength is calculated from the second set of samples using the formula Weathered Parting Strength=(G7+G8+G9+G10+G11+G12)/W2.

Where the product is mineral wool insulation it may have one or more of the following characteristics:

A density greater than 5, 8 or 10 kg/m³;

A density less than 200, 180 or 150 km/m³

Comprise glass wool fibres and have a density greater than 5, 8 or 10 kg/m³ and/or less than 80, 60 or 50 kg/m³;

Comprise stone wool fibres and have a density greater than 15, 20 or 25 kg/m³ and/or less than 220, 200 or 180 kg/m³;

A thermal conductivity λ of less than 0.05 W/mK and/or greater than 0.02 W/mK

Comprise less than 99% by weight and/or more than 80% by weight mineral fibres.

A thickness of greater than 10 mm, 15 mm or 20 mm and/or less than 400 mm, 350 mm or 300 mm.

Where the product is wood board product, it may have one or more of the following characteristics:

Dimensions of at least 50 cm×80 cm, preferably at least 1 m×2 m

Thickness of at least 11 mm, 12 mm or 15 mm

A curing time of less than 25, 15, 12 or 10 minutes

An internal bond strength measured in accordance with EN319 of at least: 0.4 N/mm² or 0.45 N/mm² (particularly for particle board or fibre boards) or measured in accordance with EN300 of at least 0.28 N/mm² (particularly for orientated strand board)

A thickness swelling after 24 hours in water at 20° C. according to EN317 of less than 12%, preferably less than 10%

A water absorption after 24 hours in water at 20° C. of less than 40%, preferably less than 30%

A modulus of elasticity according to EN310 of at least: 1800 N/mm² (particularly for particle board or fibre boards) or 2500 N/mm² (particularly for orientated strand board) or 3500 N/mm² or 4800 N/mm²

A bending strength (MOR) of at least: 14 N/m² (particularly for particle board or fibre boards) or 18 N/mm² (particularly for orientated strand board) or 20 N/mm² or 28 N/mm²

Wax as an additive, for example in the range 0.1 to 2% by weight, preferably 0.5 to 1% by weight A binder content (weight of dry resin to weight of dry wood particles) in the range 8 to 18% by weight, preferably 10 to 16% by weight, more preferably 12 to 14% by weight.

Be cured in a press, particularly between plates or platens having a temperature of greater than 180° c. or 200° C. and/or less than 280° C. or 260° C.

Various additives can be incorporated into the binder composition. These additives give the binders of the present invention additional desirable characteristics. For example, the binder may include a silicon-containing coupling agent. Many silicon-containing coupling agents are commercially available from the Dow-Corning Corporation, Evonik Industries, and Momentive Performance Materials. Illustratively, the silicon-containing coupling agent includes compounds such as silylethers and alkylsilyl ethers, each of which may be optionally substituted, such as with halogen, alkoxy, amino, and the like. In one variation, the silicon-containing compound is an amino-substituted silane, such as, gamma-aminopropyltriethoxy silane (SILQUEST A-1101; Momentive Performance Materials, Corporate Headquarters: 22 Corporate Woods Boulevard, Albany, N.Y. 12211 USA). In another variation, the silicon-containing compound is an amino-substituted silane, for example, aminoethylaminopropyltrimethoxy silane (Dow Z-6020; Dow Chemical, Midland, Mich.; USA). In another variation, the silicon-containing compound is gamma-glycidoxypropyltrimethoxysilane (SILQUEST A-187; Momentive). In yet another variation, the silicon-containing compound is an aminofunctional oligomeric siloxane (HYDROSIL 2627, Evonik Industries, 379 Interpace Pkwy, Parsippany, N.J. 07054).

The silicon-containing coupling agents are typically present in the binder in the range from about 0.1 percent to about 1 percent by weight based upon the dissolved binder solids (i.e., about 0.05% to about 3% based upon the weight of the solids added to the aqueous solution). These silicone containing compounds enhance the ability of the binder to adhere to the matter the binder is disposed on, such as glass fibers Enhancing the binder's ability to adhere to the matter improves, for example, its ability to produce or promote cohesion in non- or loosely-assembled substance(s).

In another illustrative embodiment, a binder of the present invention may include one or more corrosion inhibitors. These corrosion inhibitors prevent or inhibit the eating or wearing away of a substance, such as, metal caused by chemical decomposition brought about by an acid. When a corrosion inhibitor is included in a binder of the present invention, the binder's corrosivity is decreased as compared to the corrosivity of the binder without the inhibitor present. In one embodiment, these corrosion inhibitors can be utilized to decrease the corrosivity of the mineral fiber-containing compositions described herein. Illustratively, corrosion inhibitors include one or more of the following, a dedusting oil, or a monoammonium phosphate, sodium metasilicate pentahydrate, melamine, tin(II) oxalate, and/or methylhydrogen silicone fluid emulsion. When included in a binder of the present invention, corrosion inhibitors are typically present in the binder in the range from about 0.5 percent to about 2 percent by weight based upon the dissolved binder solids.

According to one embodiment, the fiber or particle-containing product as defined above is obtainable by the method of manufacturing a collection of matter as defined above.

According to a specific embodiment, the fiber or particle-containing product contains one or more fructosazines. Preferably, said one or more frutosazines are present in an amount of from 0.001 to 5 wt.-%, e.g. from 0.01 to 5 wt.-%, from 0.05 to 5 wt.-%, from 0.1 to 5 wt.-%, from 0.15 to 5 wt.-%, from 0.2 to 5 wt.-%, from 0.25 to 5 wt.-%, from 0.3 to 5 wt.-%, from 0.4 to 5 wt.-%, from 0.5 to 5 wt.-%, from 0.75 to 5 wt.-%, from 1 to 5 wt.-%, from 1.5 to 5 wt.-%, from 2 to 5 wt.-%, or from 2.5 to 5 wt.-%. Further examples include ranges of from 0.01 to 4.5 wt.-%, from 0.01 to 4 wt.-%, from 0.01 to 3.5 wt.-%, from 0.01 to 3 wt.-%, from 0.01 to 2.5 wt.-%, from 0.01 to 2 wt.-%, from 0.01 to 1.5 wt.-%, from 0.01 to 1 wt.-% or from 0.01 to 0.75 wt.-%. According to the present invention, the amount at which the one or more fructosazines are contained in the fiber or particle-containing product of the present invention is not limited to the above ranges, and the upper and lower values of said ranges may be freely combined.

The pre-reacted binder composition of the present invention advantageously overcomes a variety of drawbacks known from common carbohydrate-based binders. Particularly, preferred embodiments of the pre-reacted binder composition may be stored or shipped for a prolonged time without recrystallization of the carbohydrate component or gelling which would render the binder composition unusable. Moreover, preferred embodiments of the pre-reacted binder composition of the present invention results in improved cure times, improved bond strength and reduced fading, e.g. of resulting fiber products. By using preferred embodiments of the pre-reacted binder composition of the present invention, fiber or particle-containing products can be obtained which have a reduced content of unreacted carbohydrate components, so that they are more stable against microbial degradation.

The present invention will be further illustrated in the following examples, without limitation thereto.

Example 1: Pre-Reacted Binder Composition of Dextrose and Ammonia and Crosslinking with HMDA, Citric Acid and Ammonium Sulphate Dextrose was pre-reacted for various time (t=0, 1 and 3 h) at 100° C. with ammonia and subsequently cross-linked with HMDA, citric acid or ammonium sulphate. t=0 corresponds to mixing of the carbohydrate component and nitrogen-containing component and immediately adding the cross-linker i.e. without allowing any time for pre-reacting.

Calculations:

The binders were calculated with optimum molar equivalent, where sugars with half equimolar of ammonia groups are pre-reacted and cross-linked with the other half (Tables 1, 2 and 3).

The overall ratios are: C=O from sugars/-$NH_3$ from ammonia/-$NH_2$ from HMDA or $AmSO_4$ or —COOH from citric acid equals 2/1/1.

(82.76% DMH+3.92% ammonia) pre-reacted+13.32% HMDA:

TABLE 1 formulations of binders which pre-react ammonia with dextrose and are cross-linked with HMDA at alkaline pH (~11)

| Components | Formula (%) | Solids (%) | Mass (g) | Moles (mol) |
|---|---|---|---|---|
| DMH | 82.76 | 90.9 | 318.66 | 1.61 |
| Ammonia | 3.92 | 32 | 42.88 | 0.81 |
| HMDA | 13.32 | 70 | 66.60 | 0.40 |
| Water | | | 71.87 | |

(81.63% DMH+3.87% ammonia) pre-reacted+14.5% citric acid:

TABLE 2 formulations of binders which pre-react ammonia with dextrose and are cross-linked with citric acid at acidic pH (~4)

| Components | Formula (%) | Solids (%) | Mass (g) | Moles (mol) |
|---|---|---|---|---|
| DMH | 81.63 | 90.9 | 314.31 | 1.59 |
| Ammonia | 3.87 | 32 | 42.33 | 0.80 |
| Citric acid | 14.5 | 91.4 | 55.53 | 0.26 |
| Water | | | 87.84 | |

(81.22% DMH+3.85% HMDA) pre-reacted+14.93% $AmSO_4$:

TABLE 3 formulations of binders which pre-react ammonia with dextrose and are cross-linked with citric acid at neutral pH (~8)

| Components | Formula (%) | Solids (%) | Mass (g) | Moles (mol) |
|---|---|---|---|---|
| DMH | 81.22 | 90.9 | 312.73 | 1.58 |
| Ammonia | 3.85 | 32 | 42.11 | 0.79 |
| $AmSO_4$ | 14.93 | 99 | 52.78 | 0.39 |
| Water | | | 92.38 | |

Curing of Pre-Reacted Binders:

As described above, nine binders were prepared at 70% solids and diluted to 7% solids to cure them on microfiber filters. The filters were cured for 5 minutes (well cured), or 2.5 minutes (leave a slight extract in water). Also, binders were diluted at 22.5% to follow their cure rates (cf. FIG. 1). To follow cure rates, drops of binder were placed on glass fibre filters and cured for various times. The cured spots were extracted into water and the absorbance of the leachate measured using a spectrophotometer. Absorbance roses initially owing to the formation of soluble coloured compounds. The absorbance then fell due to the cross linking of these soluble compounds. The cure speed is considered to be the time taken for the absorbance to fall to the minimum value.

In this series of experiments, HMDA is the fastest cross-linker followed by ammonium sulphate and citric acid. A pre-reaction of 1 hour showed improved cure rates. Cross-linking with citric acid was slower with 3 hours pre-reaction. Ammonium sulphate and HMDA cross-linked with the same rate after 1 or 3 hours pre-reaction.

Example 2: Pre-Reacted Binder Composition of Dextrose and HMDA

Dextrose pre-reacted for 0, 15 and 60 minutes at 60° C. with HMDA and cross-linked with HMDA, citric acid or ammonium sulphate.

Calculations:

The binders were calculated based on Example 1:

The overall ratios are: C=O from sugars/-$NH_2$ from HMDA/-$NH_2$ from HMDA or $AmSO_4$ or —COOH from citric acid equals 2/0.8/0.8 (Table 4, 5 and 6).

(80% DMH+10% HMDA) pre-reacted+10% HMDA:

TABLE 4 formulations of binders which pre-react HMDA with dextrose and are cross-linked with HMDA at alkaline pH (~11)

| Components | Formula (%) | Solids (%) | Mass (g) | Moles (mol) |
|---|---|---|---|---|
| DMH | 80 | 90.9 | 308.03 | 1.55 |
| HMDA | 10 | 70 | 50.00 | 0.30 |
| HMDA | 10 | 70 | 50.00 | 0.30 |
| Water | | | 91.97 | |

(79.2% DMH+9.9% HMDA) pre-reacted+10.9% citric acid:

TABLE 5 formulations of binders which pre-react HMDA with dextrose and are cross-linked with citric acid at acidic pH (~6)

| Components | Formula (%) | Solids (%) | Mass (g) | Moles (mol) |
|---|---|---|---|---|
| DMH | 79.2 | 90.9 | 304.95 | 1.54 |
| HMDA | 9.9 | 70 | 49.50 | 0.30 |
| Citric acid | 10.9 | 91.4 | 41.74 | 0.20 |
| Water | | | 103.81 | |

(78.9% DMH+9.86% HMDA-reacted+11.24% AmSO₄:

TABLE 6 formulations of binders which pre-react HMDA with dextrose and are cross-linked with ammonium sulphate at neutral pH (~9)

| Components | Formula (%) | Solids (%) | Mass (g) | Moles (mol) |
|---|---|---|---|---|
| DMH | 78.9 | 90.9 | 303.80 | 1.53 |
| HMDA | 9.86 | 70 | 49.30 | 0.30 |
| AmSO₄ | 11.24 | 99 | 39.74 | 0.30 |
| Water | | | 107.17 | |

Figure 2:
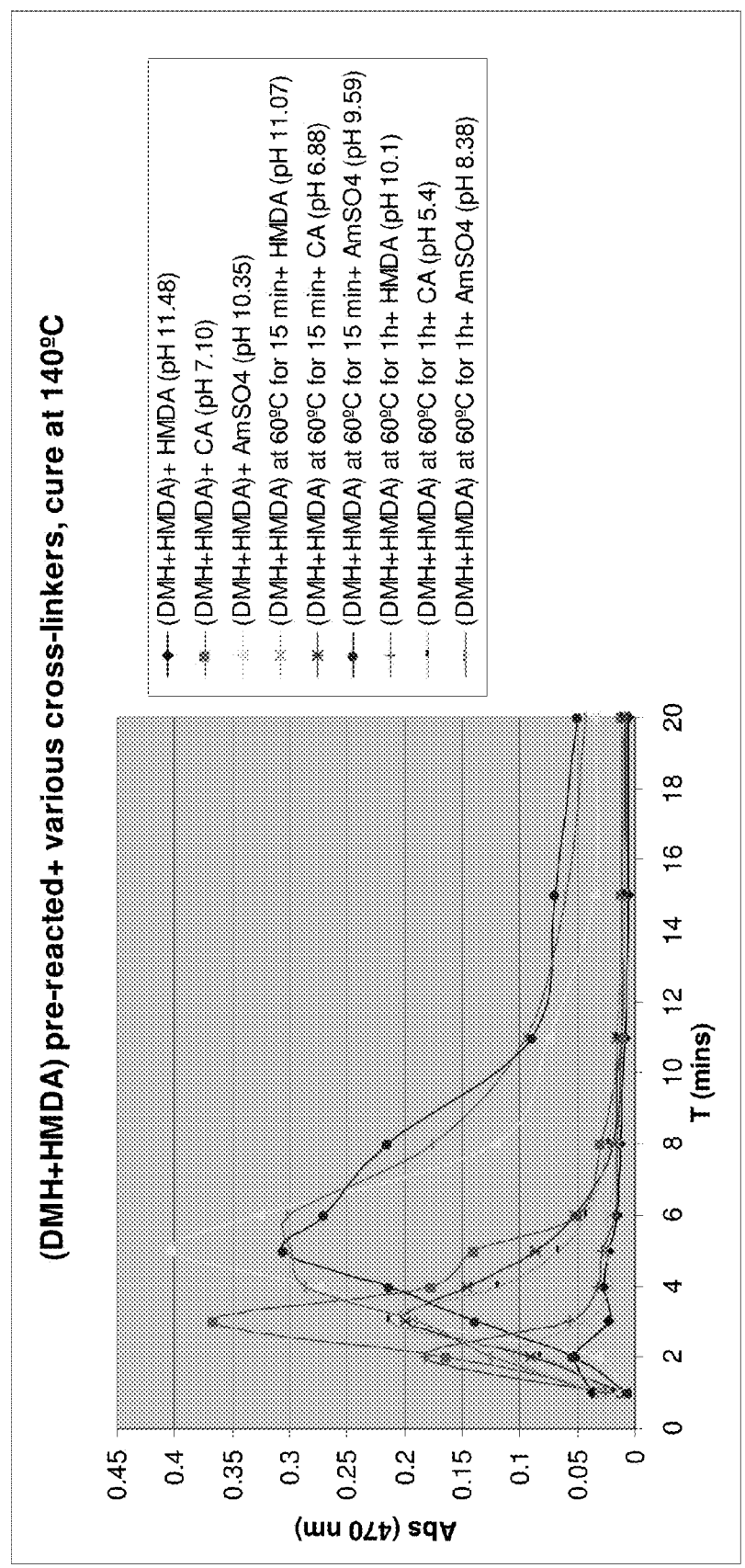
FIG. 2 shows: Cure rates of dextrose binders pre-reacted with HMDA and their pH.

Curing of Pre-Reacted Binders:

As described in section Example 1, binders were cured on filters (for 5 minutes at 200° C.) and in aluminium dishes. Their cure rates were compared at 140° C. (cf. FIG. 2) using the procedure described with respect to Example 1 for following cure rates.

In this series of experiments, when Dextrose and HMDA are pre-reacted, HMDA is still the fastest cross-linker followed by citric acid and ammonium sulfate. This suggests that the polymers formed via the pre-reaction with HMDA are different than the ones formed with ammonia, hence citric acid becomes a more efficient cross-linker than ammonium sulphate.

Example 3: Ageing Study on Pre-Reacted Binder Composition

Purpose

To assess how pre-reacted binders change over time with regards to particleboard production. In particular, provides an indication as to whether an aged pre-reacted binder produces boards of better or worse Internal Bond Strength (IB) and the effect on the degree of swelling versus use of a fresh pre-reacted binder.

Introduction

It can take a few weeks from the initial production of a binder until its use in lab or plant trials. This is mainly due to shipping times, manufacturing schedules and test delays. It is necessary to know whether ageing of binder by a few weeks affects the properties of any boards made from it. It is believed that the pre-reacted binder will keep on reacting at a much lower speed at room temperature (~20° C.), which may result in i) a continuation of the Maillard reaction towards melanoidins, meaning that the final cure has less reactions to accomplish and as such, should be quicker and easier to achieve, ii) the reaction could proceed somewhat down different pathways making molecules that when bound as melanoidins are stronger or possibly weaker when fully cured, and iii) these extra reactions could be producing unwanted side products such as acids, which may slow down the cure.

Method 1.8 kg pre-reacted binder was made, consisting of:
616 g Dextrose,
560 g Fructose,
200 g HMDA and
424 g Water.

Pre-reaction was controlled for 15 minutes at 60-63° C. To this an extra 200 g HMDA would need to be added to make 2 kg of binder. The extra amount of HMDA actually needed per mix was calculated and added as and when needed to the required amount of pre-react. No extra HMDA was added to the bulk of the pre-react at any time.

Boards were made the day after the pre-reacted binder was made, and every 7 days from that point on. Viscosity of the pre-reacted binder and gel time of binder produced from it were measured when boards were made. Two boards were made with each mix by pressing and curing between platens of a press under the following conditions:
Board size—300 mm×300 mm×10 mm
Desired density—650 kg/m³
Moisture of chips—3.1%
% Binder—10.0% by weight
Platen temperature—195° C.
Press factor—14 s/mm
Pressure—504 KN Assuming the first mix to be at day 0, boards were produced at day 0, 7, 14 and 21. At days 0 and 14, only one board was tested, as at day 0, one board was made at 12 s/mm and at day 14, one board was used to trial a new procedure.

After production, boards were conditioned under similar conditions for a minimum of 3 days before testing. Testing consisted of internal bond tests on a Testometric machine, and both 2 hour and 24 hour swelling tests in a water bath set to 20° C.

Results:

TABLE 7

Figure 3:
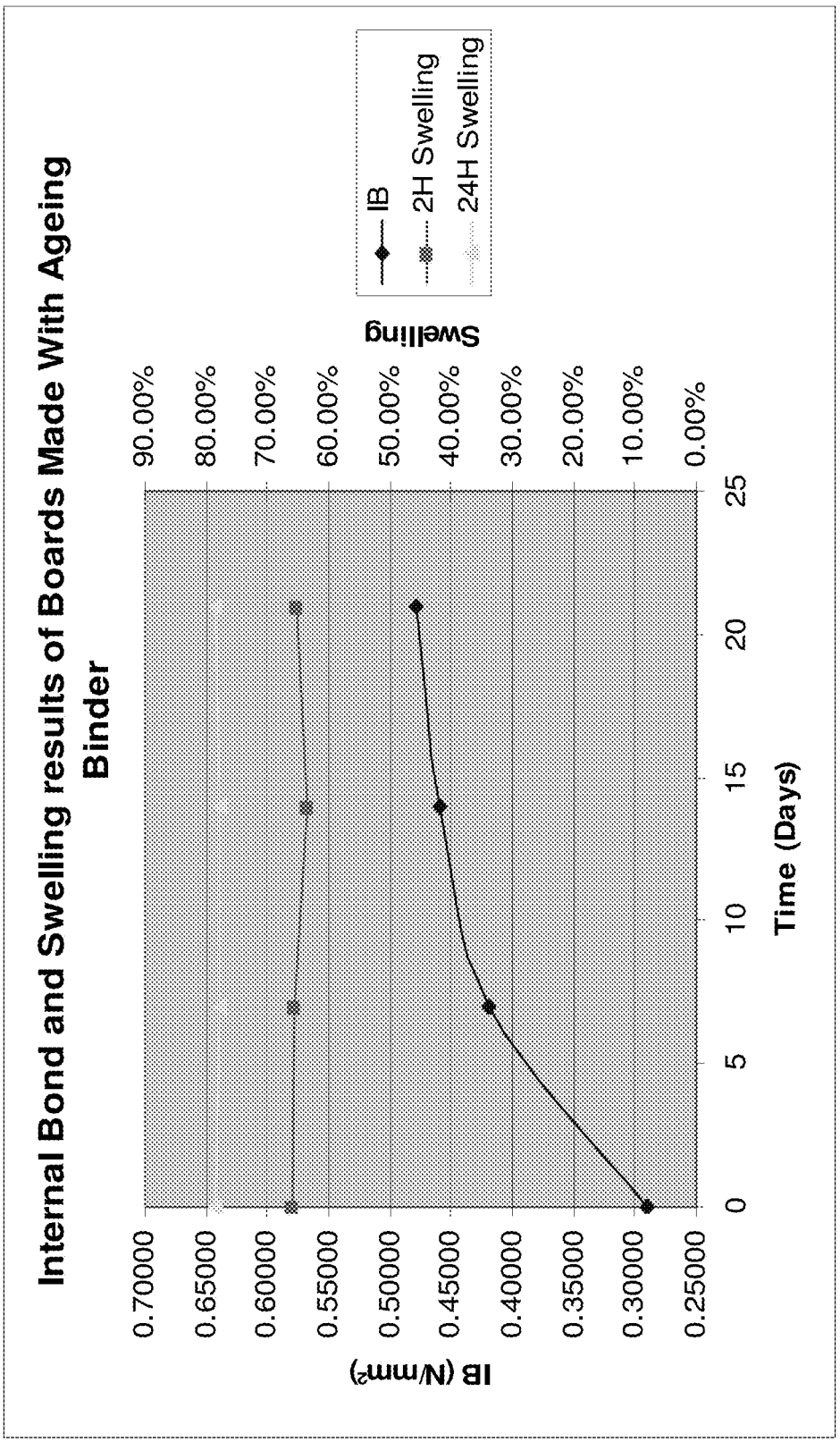
FIG. 3 shows: An average internal bond and swelling results for boards made with a dextrose/fructose+HMDA pre-reacted binder at differing ages.
Figure 4:
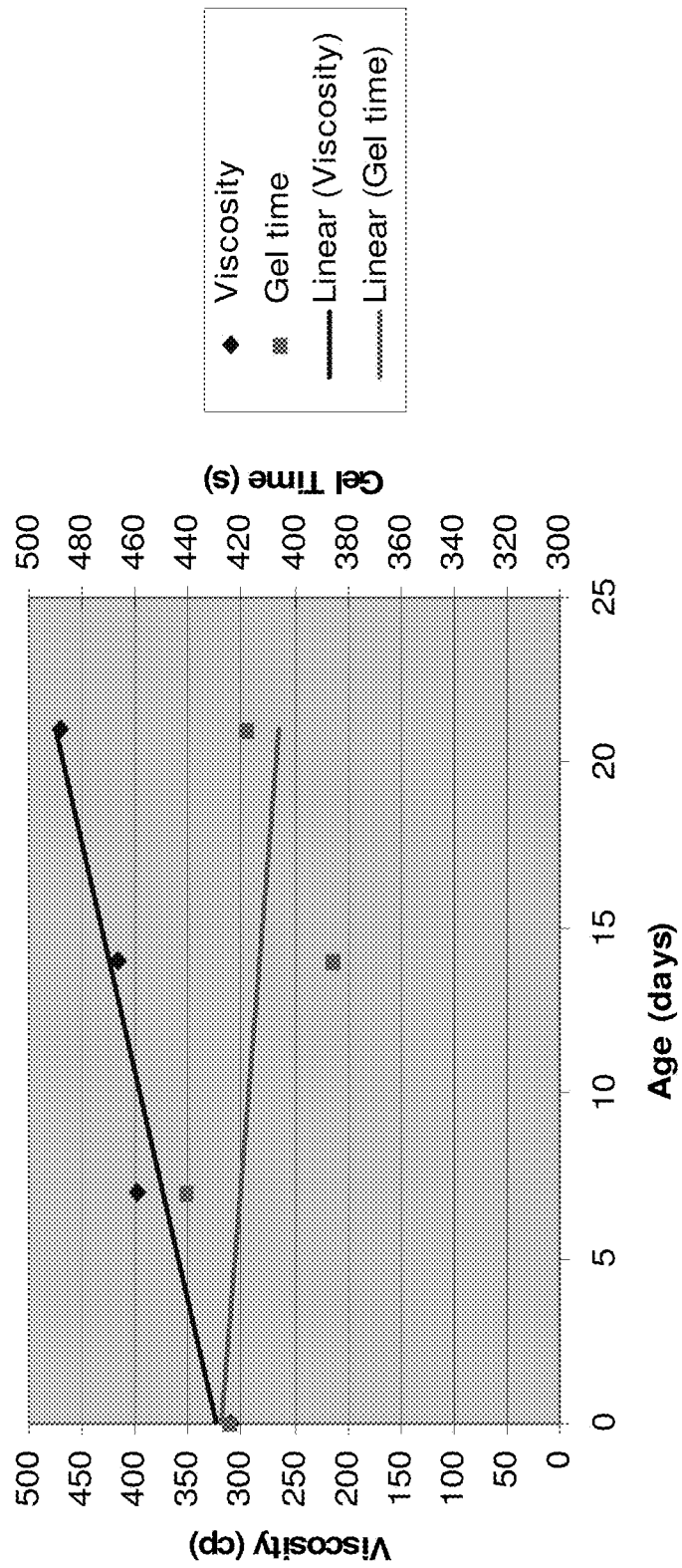
FIG. 4 shows: Viscosity and geltime of an aging dextrose/fructose+HMDA prereacted binder, measured on the same day as boards were made.

Results of internal bond and swelling tests (also cf. FIG. 3)

| Age (Days) | IB (N/mm²) | Swelling 2 h | Swelling 24 h |
|---|---|---|---|
| 0 | 0.29081 | 65.87% | 78.56% |
| 7 | 0.41936 | 65.62% | 77.70% |
| 14 | 0.45989 | 63.62% | 77.95% |
| 21 | 0.47871 | 65.11% | 78.61% |

Example 4: Preparation Method for Manufacturing Pre-Reacted Binder Compositions

A pre-reacted binder composition may be manufactured by the following procedure:
1. Add required quantity of hot water to required quantity of sugar(s).
2. Record total weight of beaker, solution and stirring rod.
3. Apply heat and stirring to assist dissolving. A hot plate and electric stirrer work well. This can take 30 minutes or longer. Make sure all crystals have dissolved and solution is clear.
4. Temperature of carbohydrate (e.g. dextrose) solution should be around 55° C.–60° C. once dissolved. If not then adjust it to meet.
5. Check weight of beaker, solution and stirrer and top up to recorded weight in (2.) with water, to account for evaporation.
6. Add required amount of nitrogen-containing component (e.g. HMDA) and record new total weight, then apply stirring.
7. Reaction temperature should rise to 60° C. and it should be maintained between 60-63° C., using a hot plate if necessary.
8. Hold at temperature for 15 minutes, stirring constantly with electric stirrer. Solution should turn yellow→brown→very dark brown.
9. Check weight and top up to weight recorded in (6.), to account for evaporation.

10. Cool solution quickly in loosely sealed containers, to avoid as much evaporation as possible. A water bath works well, as does splitting solution into multiple parts to aid cooling. It is important that the reaction mixture is cooled before use, and potential evaporation reduced.
11. Once cooled, the pre-reacted solution is complete. Viscosity at 20° C. should be in the region of 300-320 cp.

Example 5: Stability of Xylose:Fructose+HMDA Pre-Reacted Binders

Without pre-reaction, when combining a carbohydrate solution containing 50% xylose, gelling generally occurs within 5 minutes. Accordingly, the manufacture of boards from using such a binder is impossible. With pre-reaction, however, it is possible to make a stable binder which was successfully used to create wood boards.

Table 8 shows the results of testing stability of a pre-reacted binder (Xylose:Fructose:HMDA 44.44:44.44:11.11 by % weight of reactant). Table 9 shows the results of testing stability of these pre-reacted binders following a further addition of HMDA after the pre-reaction has been carried out to give total reactant contents by weight of Xylose:Fructose:HMDA/40:40:20 (which can also be expressed as: pre-reacted (Xylose:Fructose:HMDA)+subsequently added HMDA (40:40:10)+10). Different pre-reaction times were tried.

TABLE 8

Showing stability of Xylose: Fructose pre-reactions, heated for different lengths, over time. Little difference was observed in pre-reactions above 15 minutes. Viscosity work and water content analysis required to show greater differences.

| Pre-reacted for | Stability at time | | | |
|---|---|---|---|---|
| (min) | Day 0 | Day 1 | Day 2 | Day 3 |
| 7.5 | Stable | Gelled | | |
| 15 | Stable | Stable | Slight thickening | Thickening |
| 22.5 | Stable | Stable | Slight thickening | Thickening |
| 30 | Stable | Stable | Slight thickening | Thickening |
| 37.5 | Stable | Stable | Slight thickening | Thickening |

TABLE 9

Showing stability of Xylose: Fructose binders, following pre-reaction and 2$^{nd}$ HMDA addition, based on different pre-reactions (see Table 8).

| Pre-reacted for (min) + subsequent addition of HMDA | Stability at time | | | |
|---|---|---|---|---|
| | Day 0 | Day 1 | Day 2 | Day 3 |
| 15 | Stable | Gelled | | |
| 22.5 | Stable | Stable | Stable | Cured |
| 30 | Stable | Stable | Stable | Cured |
| 37.5 | Stable | Stable | Stable | Cured |

In this series of experiments, little difference was shown in binders created from 22.5 minute pre-reacted binder solutions and above. It can be noted that the binder made from the 15 minute pre-reaction had gelled, whereas the other binders had cured.

The above work on xylose binder stability has shown that a pre-reaction time of 22.5 minutes is the lowest known to create a stable binder. The actual point lies somewhere between 15 and 22.5 minutes. The curing speed shown by xylose binders is clearly visible here as the binder cured at room temperature in 3 days.

Example 6: Comparison of Pre-Reacted Binder with Conventional Binder

In this series of experiments, the binder recipe was as follows:

85% DMH (dextrose monohydrate)+15% AmSO$_4$ (ammonium sulfate)+1.25% NH$_4$OH+9% oil emulsion+0.3% ISI0200 (silane)

For pre-reacted binder, DMH and AmSO$_4$ were pre-reacted for 2 hours at 100° C. with 65% solids. On the day of the trial, this binder was diluted; ammonia, oil emulsion and silane were added to it.

240 kg of pre-reacted binder (65% solids) were prepared in the lab. On the day of the trial, this binder was diluted, silane and oil emulsion were also added to give a binder solids of 15%.

The non-reacted binder was made by combining the ingredients on the day of the trial without heating.

The binders were used in the manufacture of a 25 mm thick mineral wool insulation (universal slab CS32), density=32 kg/m$^3$, with a binder content (% wt measured as LOI)=7.5%.

It was found that the pre-reacted binder gave a product which was more rigid and dustier than with a standard non-pre-reacted binder. Increase in dustiness could indicate the binder has been overcured. The cure and binder content (% weight measured as LOI) with the pre-reacted and non-prereacted binder were similar. The pre-reacted binder also faded less when exposed to light which shows the pre-reacted polymer gives a different chromophore (cf. FIG. 5).

Table 10 below shows that:

i) Both binders gave a glass wool insulation product having similar LOI, cure and parting strength. The pre-reacted binder was more rigid and dustier. The increase in dusts can be perhaps partially explained by a higher density for the product made with the pre-reacted binder.

ii) The ramp moisture varies in places of the mat which may be due to an imbalance of the suction under the forming conveyor.

TABLE 10

Comparison of Standard binder with pre-reacted binder

| Binder | Ramp moisture | LOI/% | Cure | Rigidity (gap = 100 cm) | Rigidity (gap = 80 cm) | Dust | Density (kg/m$^3$) | Parting strength g/g |
|---|---|---|---|---|---|---|---|---|
| Standard (non- | Left: 5.52% | 7.63 | 0.09 | 3 slabs: m = 1.7 kg, | 1 slab: m = 0.57 kg, | 0.43 g/kg 12.42 g/m$^3$ | 31.42 | 273.26 |

TABLE 10-continued

Comparison of Standard binder with pre-reacted binder

| Binder | Ramp moisture | LOI/% | Cure | Rigidity (gap = 100 cm) | Rigidity (gap = 80 cm) | Dust | Density (kg/m³) | Parting strength g/g |
|---|---|---|---|---|---|---|---|---|
| pre-reacted) | | | | Drop: 48.1 cm | Height: 65.5 cm | | | |
| Pre-reacted | Right: 9.54% Left: 5.51% Right: 7.39% | 7.02 | 0.09 | 3 slabs: m = 1.8 kg, Drop: 31.1 cm | 1 slab: m = 0.60 kg, Height: 67.8 cm | 0.44 g/kg 15.42 g/m³ | 33.23 | 282.33 |

Figure 5:
FIG. 5 shows: The pre-reacted binder (GWE2) fading less than standard binder (GWST) during Weatherometer exposure testing with 327 hours under Xenon light.
Figure 6:
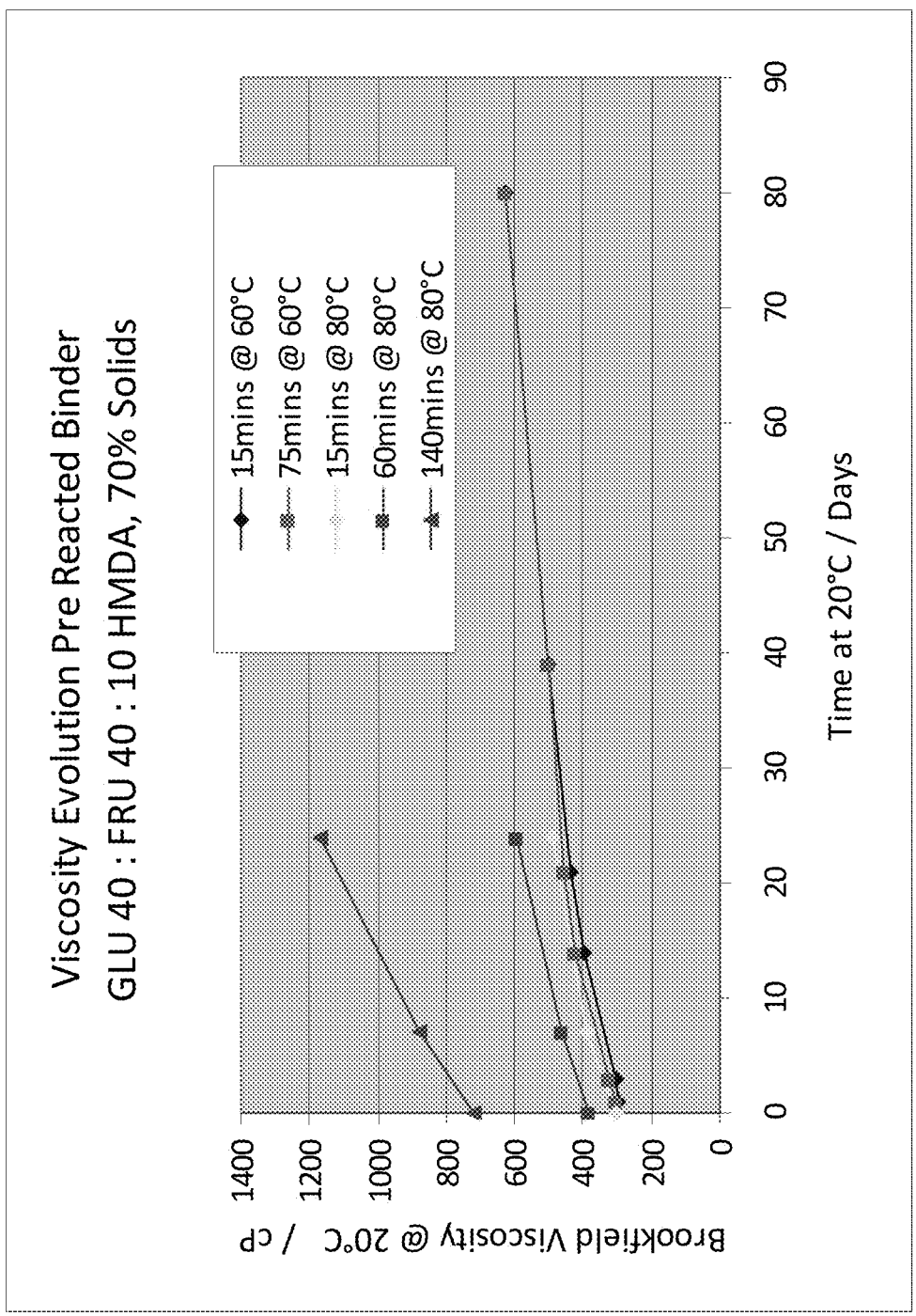
FIG. 6 shows: Viscosity evolution for various pre-reacted binders.
Figure 7:
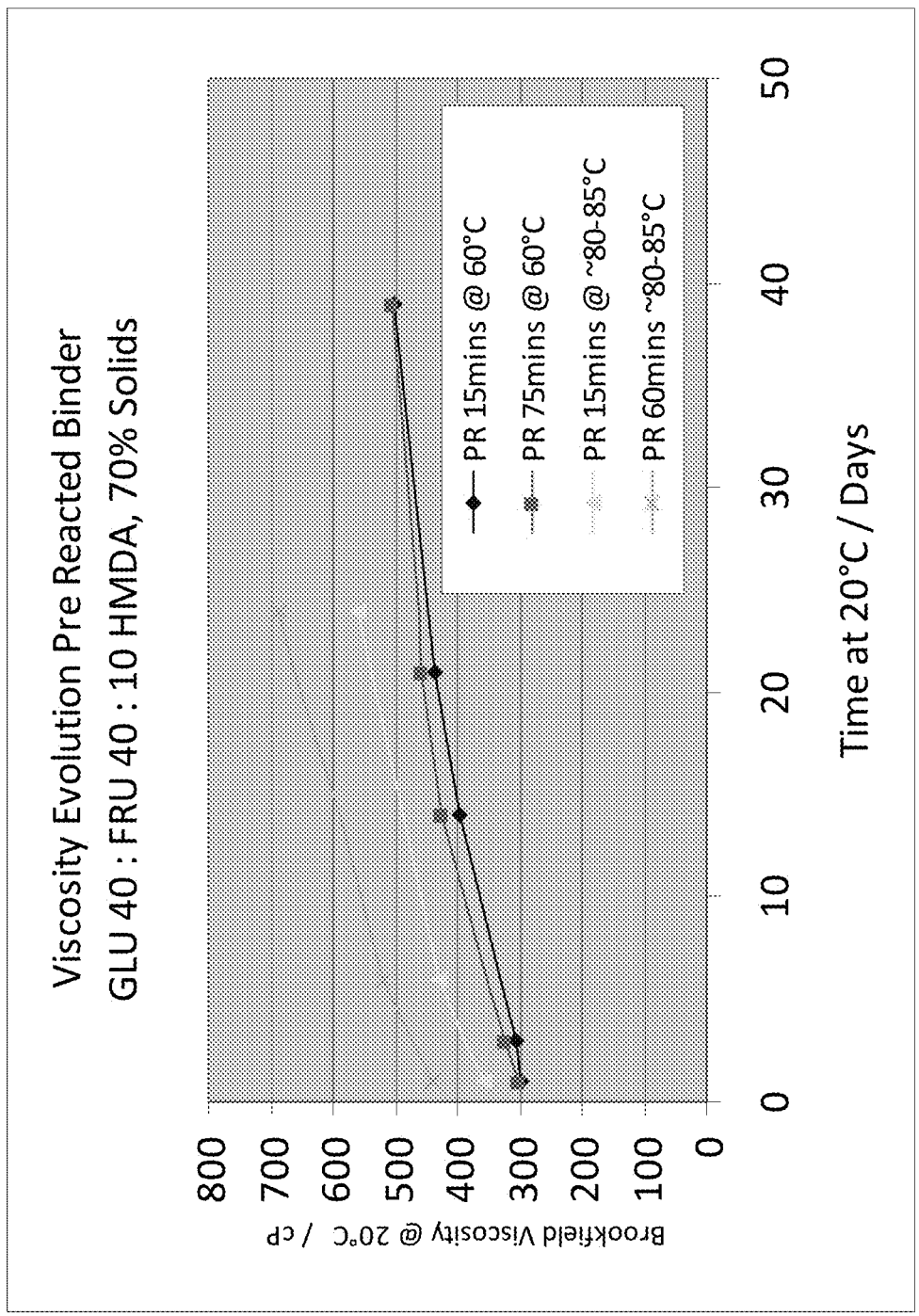
FIG. 7 shows: Viscosity evolution for various pre-reacted binders.
Figure 8:
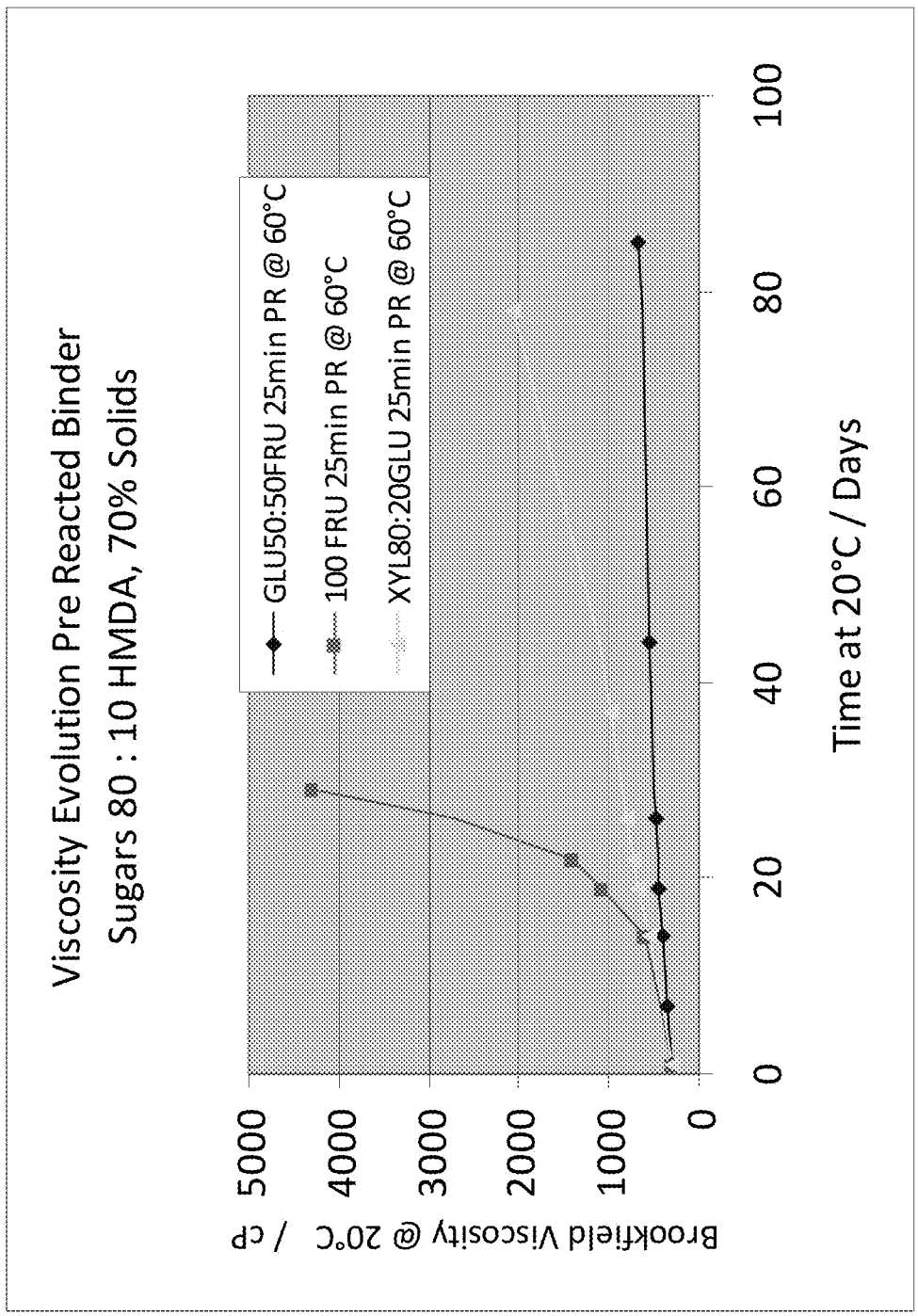
FIG. 8 shows: Viscosity evolution for various pre-reacted binders.
Figure 9:
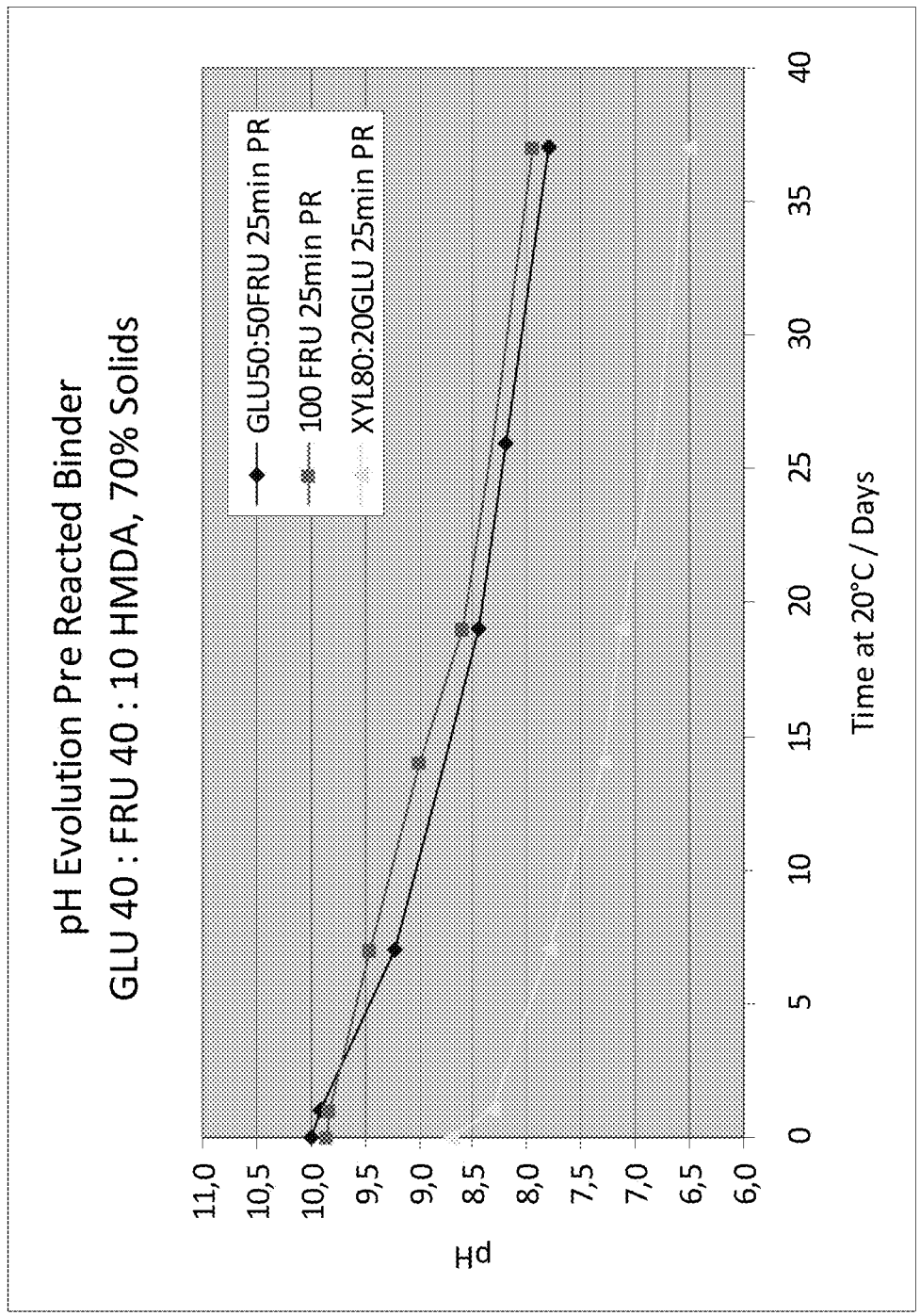
FIG. 9 shows: pH evolution for various pre-reacted binders.
Figure 10:
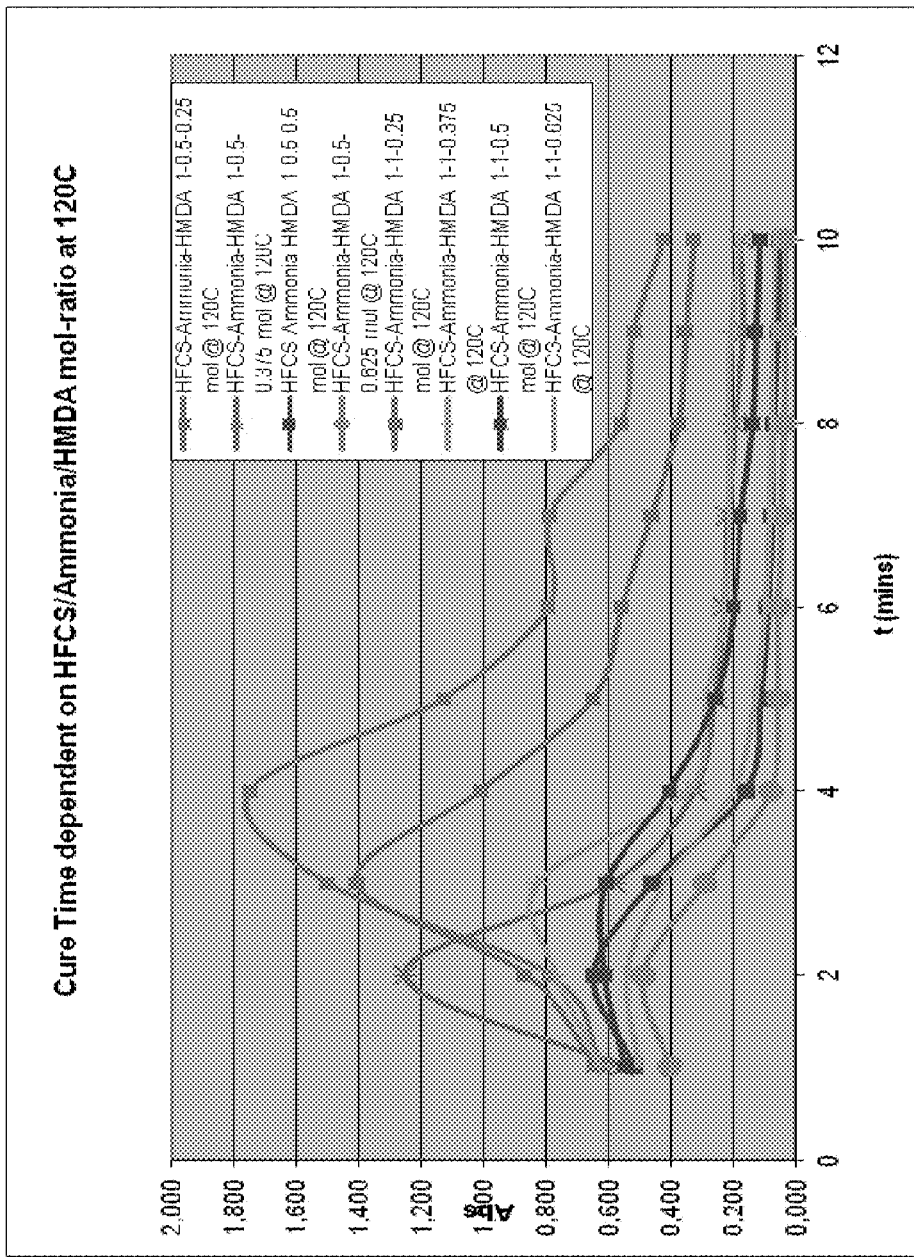
FIG. 10 shows: Cure Time dependent on HFCS/Ammonia/HMDA mol ratio at 120° C. cure temperature.
Figure 11:
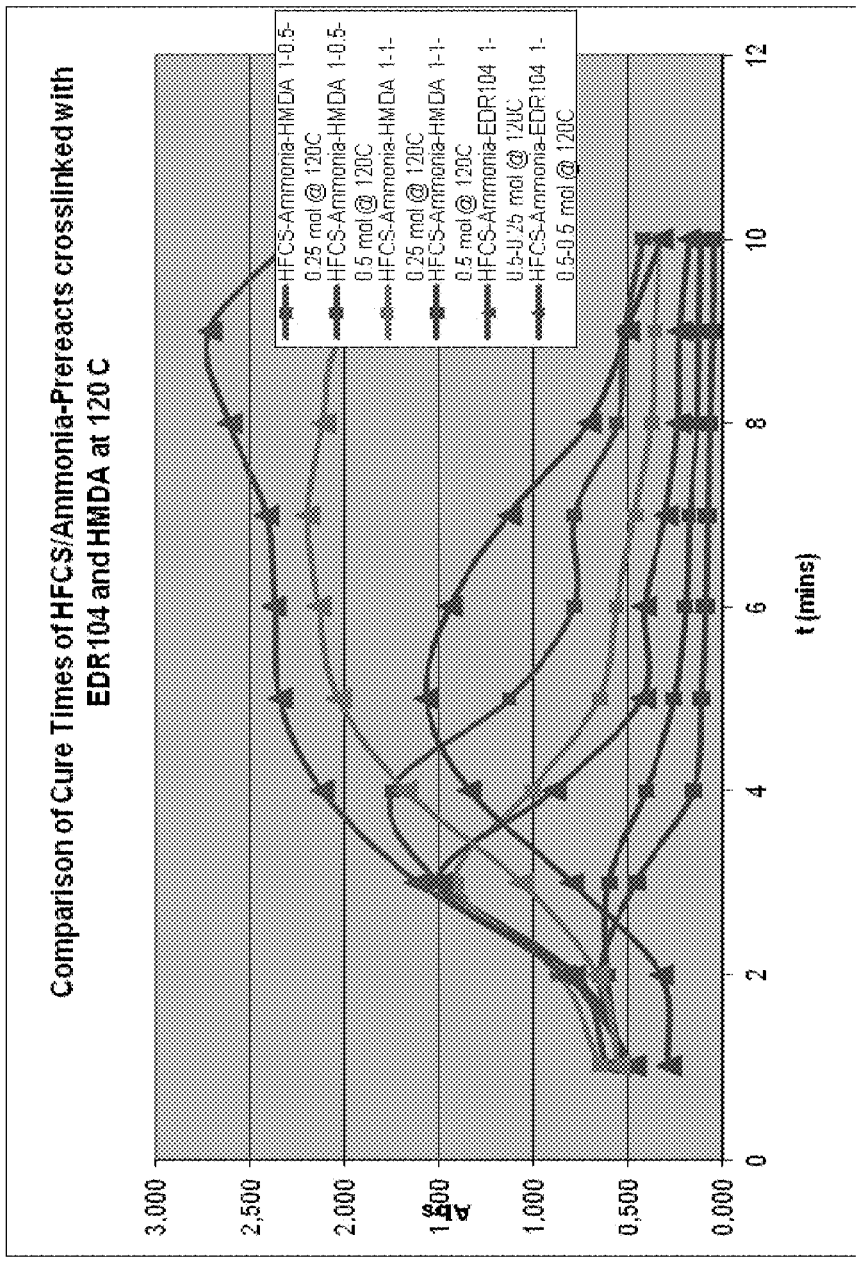
FIG. 11 shows: Cure Times of HFCS/Ammonia-prereacts crosslinked at 120° C. dependent on diamine (HMDA vs. EDR-104)
Figure 12:
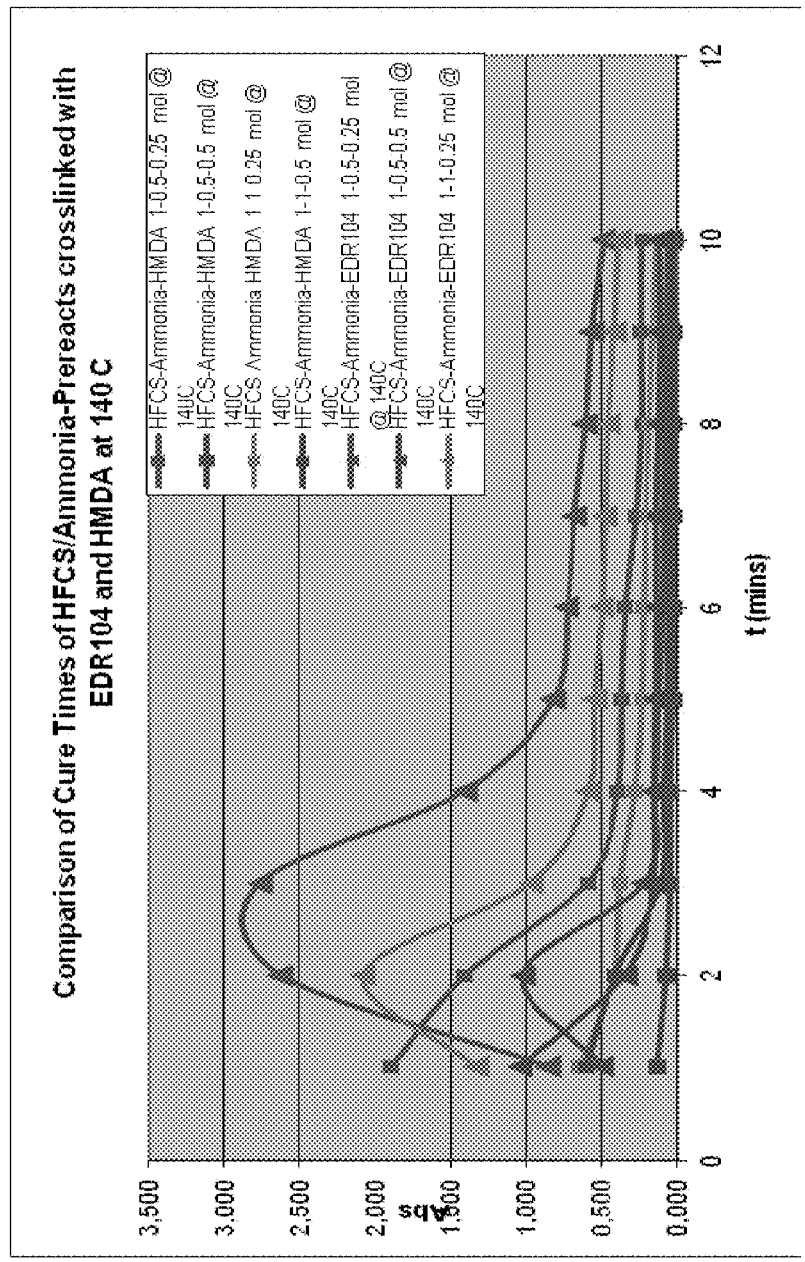
FIG. 12 shows: Cure Times of HFCS/Ammonia-prereacts crosslinked at 140° C. dependent on diamine (HMDA vs. EDR-104)
Figure 13:
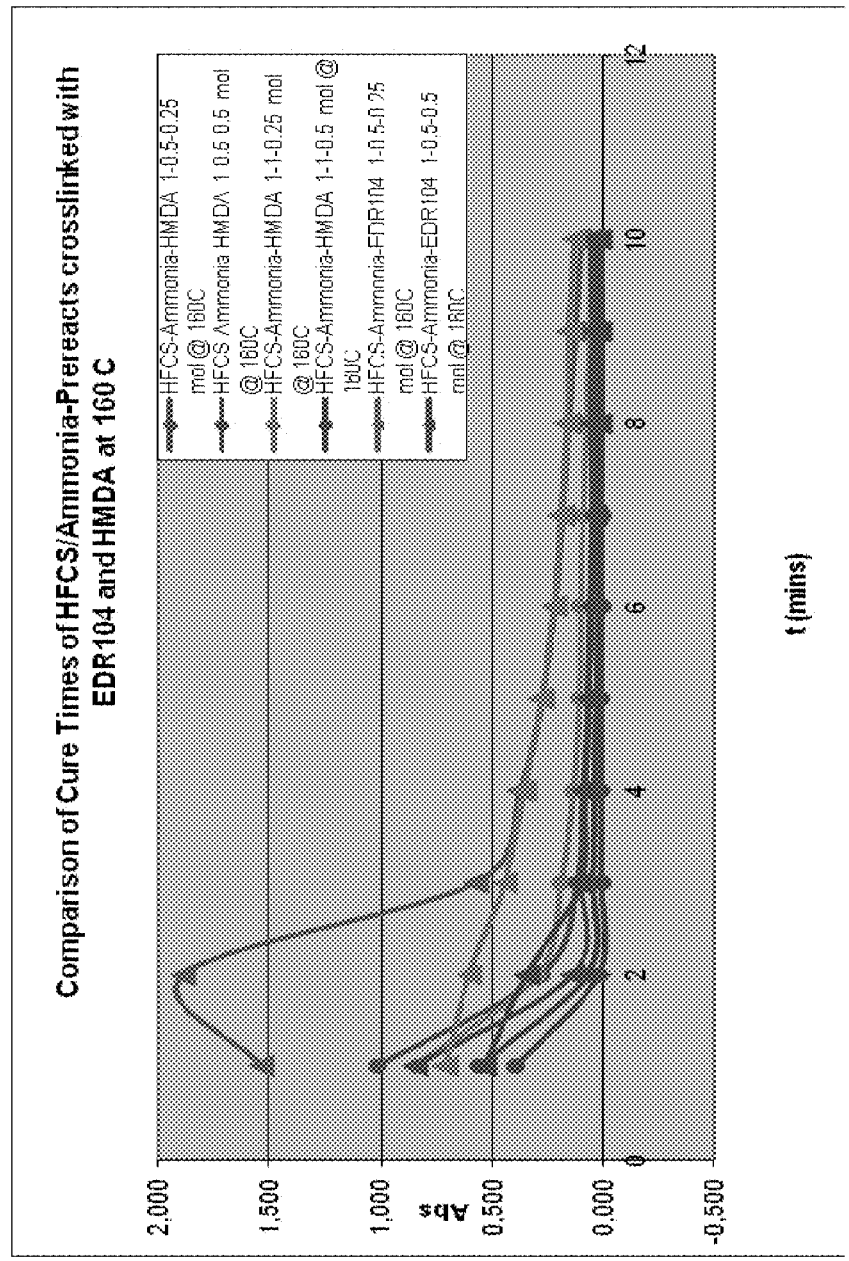
FIG. 13 shows: Cure Times of HFCS/Ammonia-prereacts crosslinked at 160° C. dependent on diamine (HMDA vs. EDR-104)

FIG. 5 shows the pre-reacted binder (GWE2) fades less than standard binder (GWST) during Weatherometer exposure testing with 327 hours under Xenon light. This time of exposure is representative of four months exposure in the U.K.

The pre-reacted binder showed an advantage in rigidity of the manufactured product. Other potential advantages of having the DMH pre-reacted are less recrystallisation before the curing oven and decrease of bacteria level in wash water. The fading experiments showed that the pre-reacted binder fades less.

Example 7: Viscosity of Pre-Reacted Binder Compositions

Pre-Reacted Binder Preparation:

DMH/HMDA Prereacts were prepared by mixing DMH (88.89 wt.-%, based on the total weight of the binder composition without water) and HMDA (11.11 wt.-%, based on the total weight of the binder composition without water), i.e. 5.16 molar equivalent of DMH and 1 molar equivalent of HMDA, in water (at 70% solids) in a sealed pressure glass bottle and heated at 60° C. for 20 min to prepare a pre-reacted binder composition.

Figure 15:
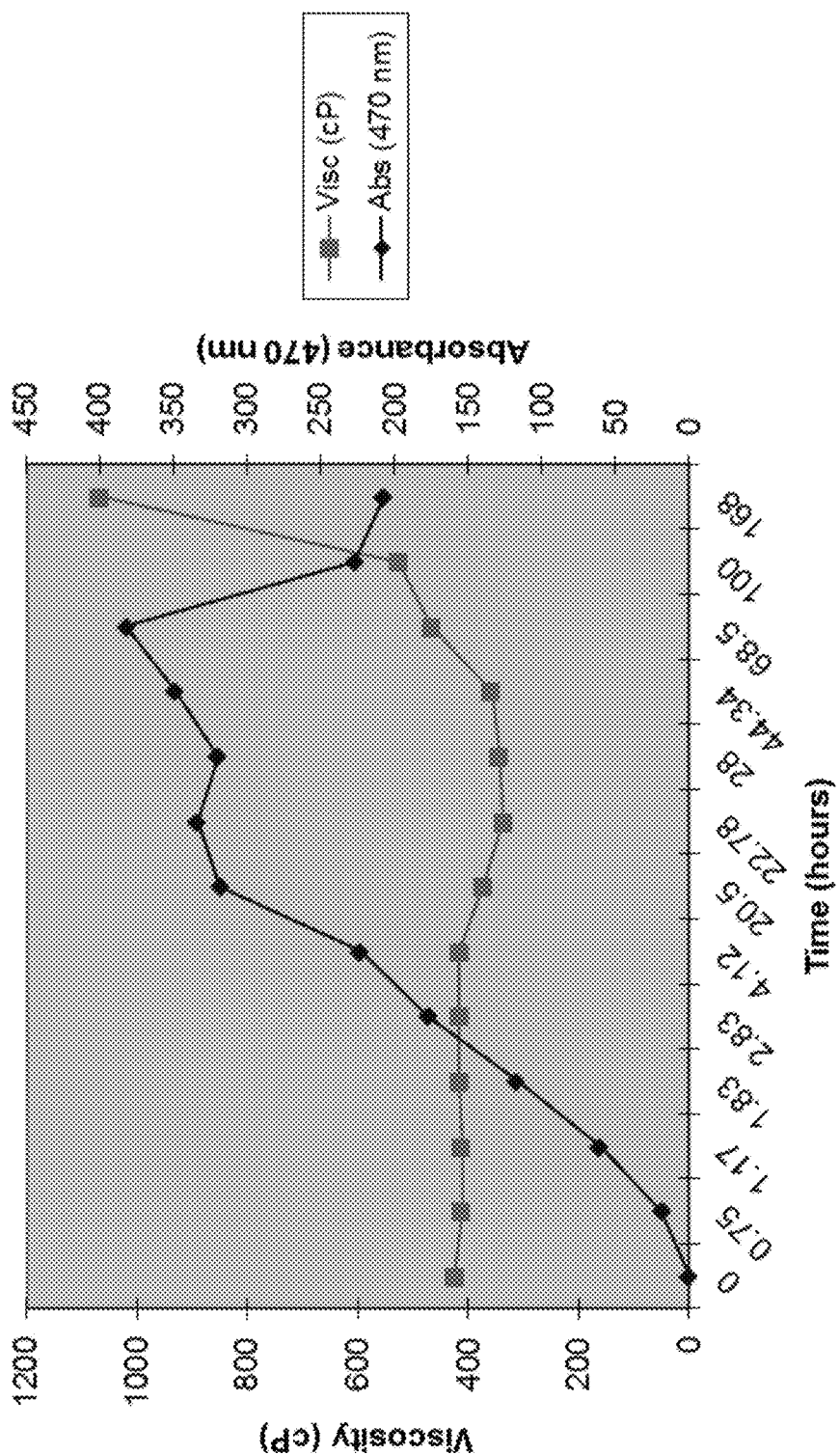
FIG. 15 shows: Viscosity and absorbance of a pre-reacted binder composition.

The pre-reacted binder composition was further heated for 11 days at 60° C. while following the viscosity and adsorbance of the binder solution. As shown in FIG. 15, in this series of experiments only absorbance of the prereact steadily increased over pre-reaction time, while the viscosity of the prereact did not increase until the latest stage of the pre-reaction.

Example 8: GPC Analysis of Various Pre-Reacted Binder Compositions

Configuration of GPC Analysis:
HPLC Configuration

| Pump | Shimadzu LC-9A |
|---|---|
| Autosampler/system controller | Shimadzu SIL-6B/Shimadzu SCL 6B |
| Communications bus module | Shimadzu CBM-10A |
| Refractive index detector | Shimadzu RID-6A |
| Diode array detector | Shimadzu SPD-M10A |
| Evaluation software | Shimadzu Class LC-10 |

Method Configuration

| Column temperature | 20° C. |
|---|---|
| Concentration gradient | Isocratic |
| Solvent | Water (deionised) |
| Flow | 1 ml/min |
| Analysis time | 35 min |

GPC Columns

| Pre-column | Agilent, GPC/SEC Guard Columns, PL aquagel-OH Guard, 8 µm, 50 × 7.5 mm |
|---|---|
| 1. Column | TosoHaas, TSKGel G 3000, 10 µm, 300 × 7.5 mm |
| 2. Column | TosoHaas, TSKGel G 4000 PWXL, 10 µm 300 × 7.8 mm |

Figure 16:
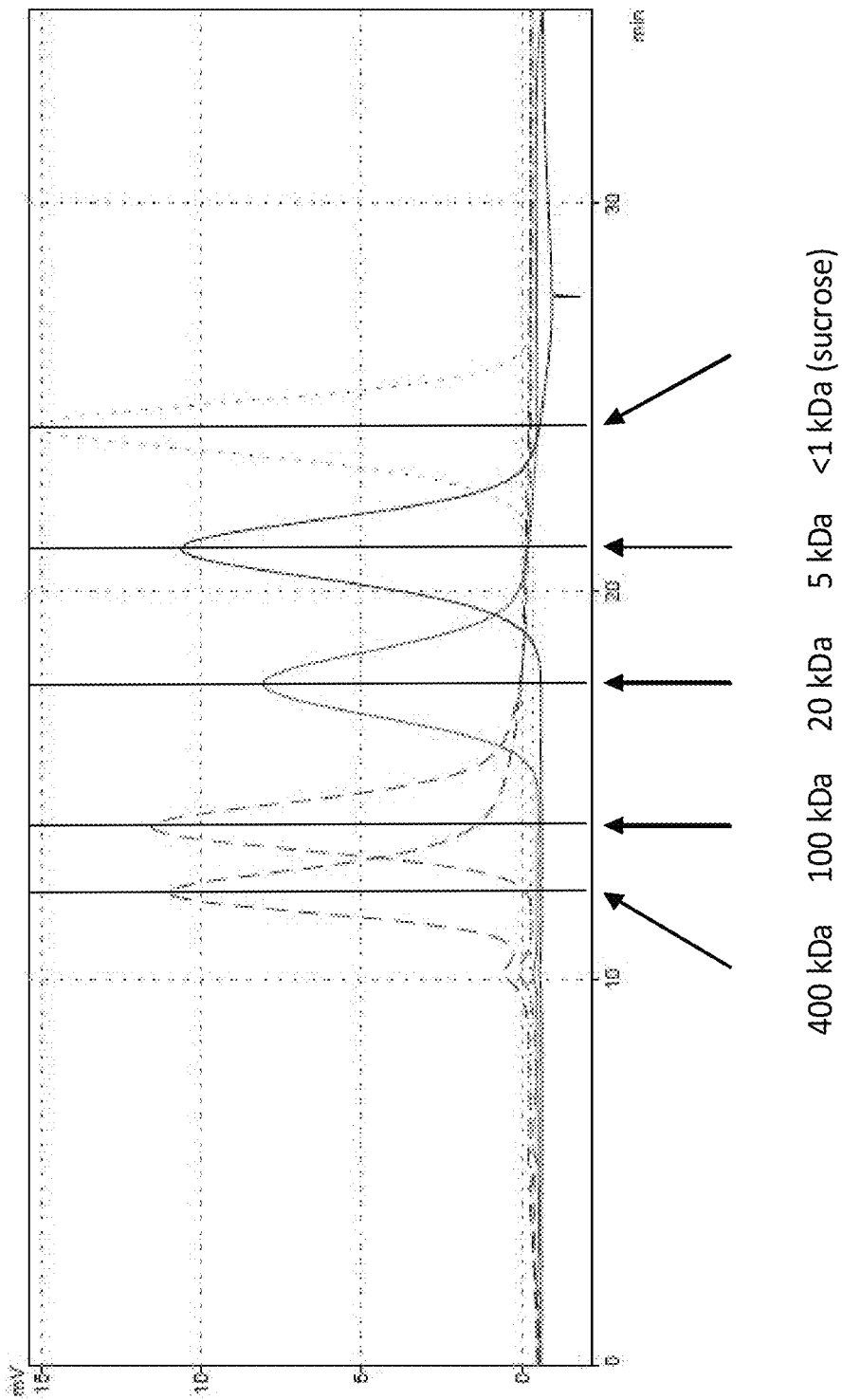
FIG. 16 shows: Calibration of the GPC device.

The above-described GPC device was calibrated using sucrose and various pullulans (FIG. 16).

D-Glucose (44.45 wt.-%, based on the total amount of binder composition without water), D-fructose (44.45 wt.-%, based on the total amount of binder composition without water) and HMDA (11.1 wt.-%, based on the total amount of binder composition without water) were mixed in water to obtain a binder composition.

Figure 17:
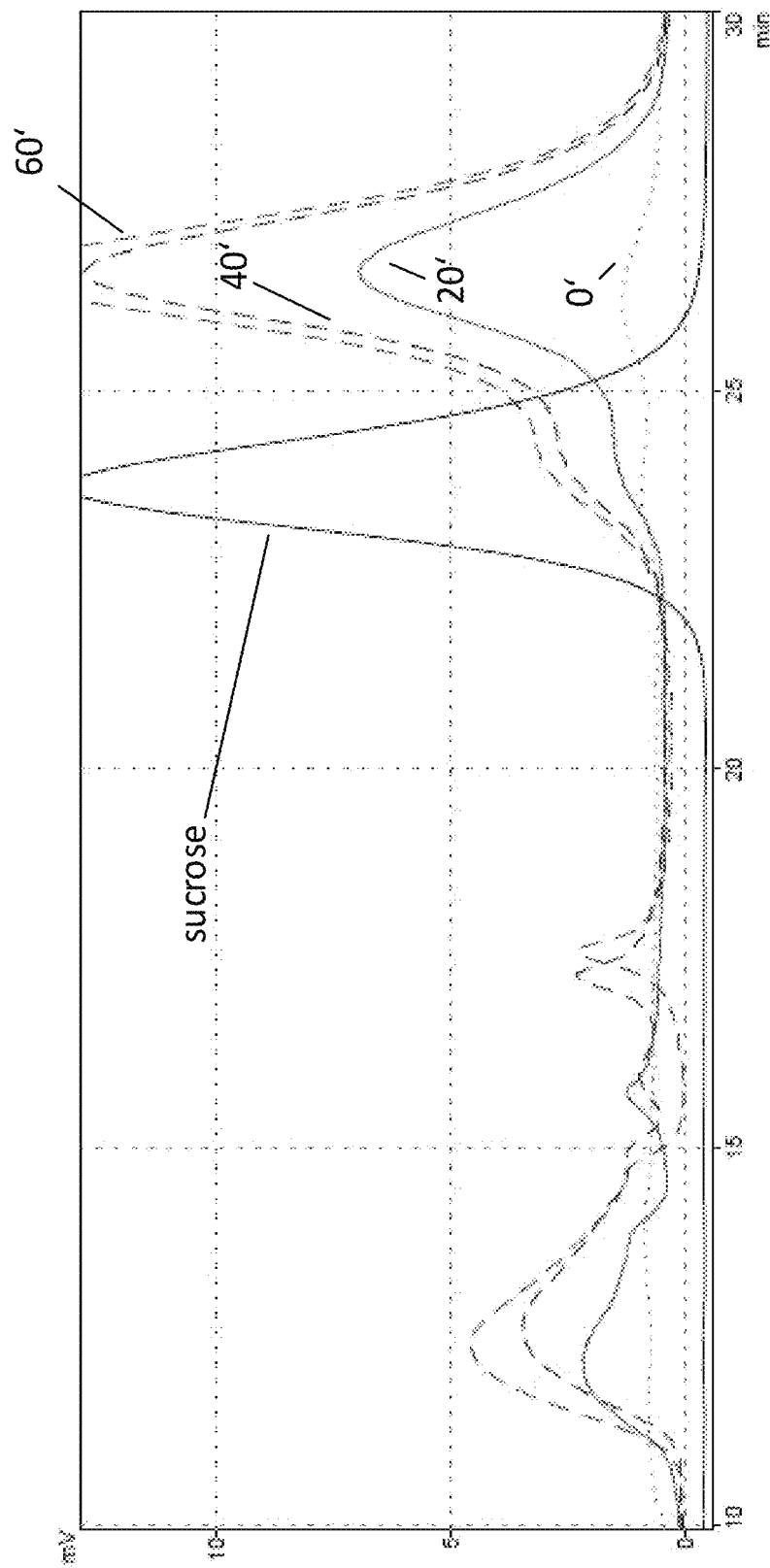
FIG. 17 shows: GPC chromatograms of pre-reacted binder composition with various pre-reaction times.

GPC Analysis after Various Pre-Reaction Durations:

FIG. 17 shows GPC chromatograms (standard: sucrose) of the above binder composition when pre-reacted at 60° C. for 0 min, 20 min, 40 min and 60 min.

The GPC diagram clearly shows the presence of pre-polymers having a relatively high molecular weight (GPC retention of approximately 10 to 15 minutes), of mid-molecular weight pre-polymers (GPC retention of approximately 15 to 20 minutes) and the low molecular fraction of the prereacted binder composition (GPC retention approximately >20 minutes).

Figure 18:
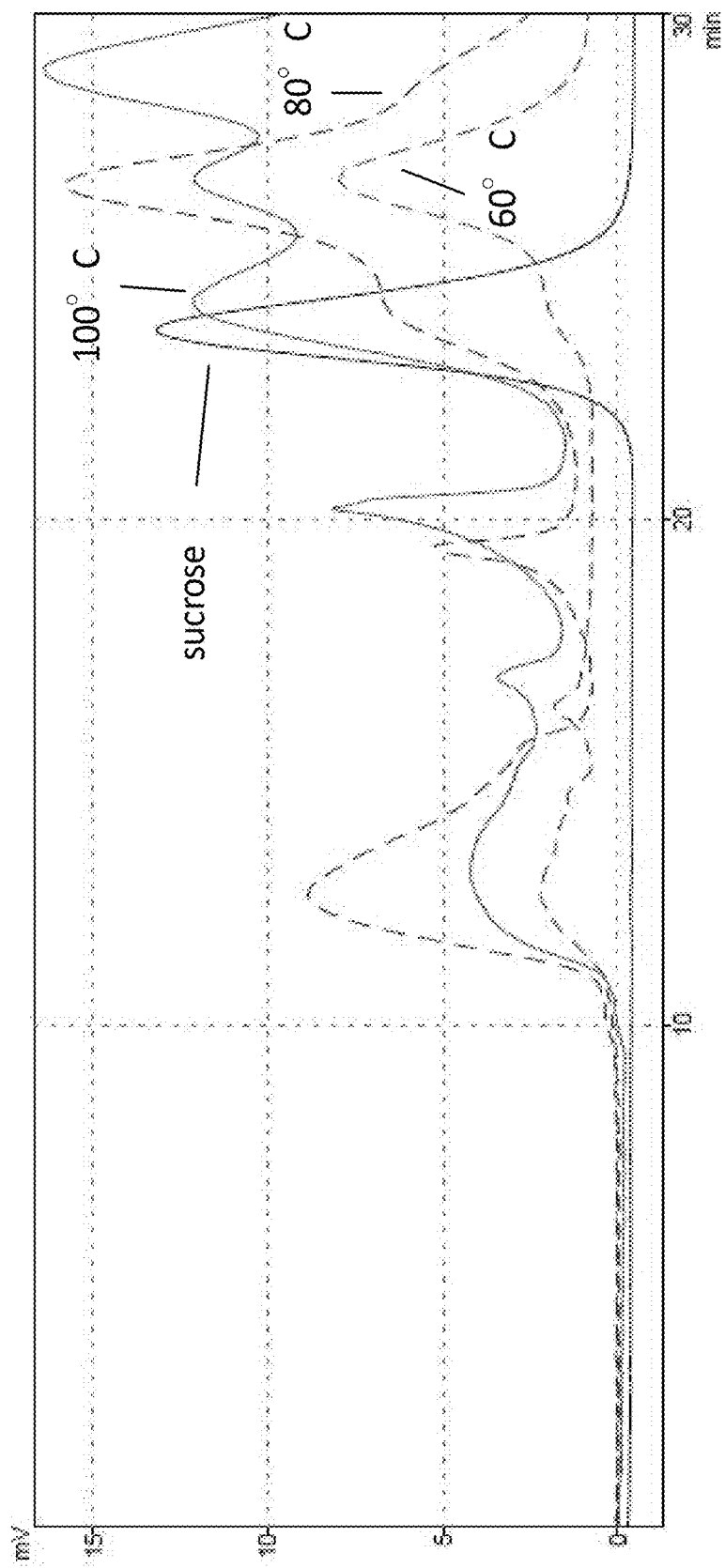
FIG. 18 shows: GPC chromatograms of pre-reacted binder composition with various pre-reaction temperatures.

GPC Analysis at Various Ore-Reaction Temperatures:

FIG. 18 shows GPC chromatograms (standard: sucrose) of the above binder composition when pre-reacted for 20 min at 60° C., 80° C. and 100° C.

The GPC diagram clearly shows the presence of pre-polymers having a relatively high molecular weight (GPC retention of approximately 10 to 15 minutes), of mid-molecular weight pre-polymers (GPC retention of approximately 15 to 20 minutes) and the low molecular fraction of the prereacted binder composition (GPC retention approximately >20 minutes).

What is claimed is:

1. A method of manufacturing a collection of matter bound by a polymeric binder comprising: (i) providing a collection of matter; (ii) providing a water-soluble prereacted binder composition in the form of an aqueous solution or dispersion, the aqueous solution or dispersion containing no more than 80 wt.-% of said pre-reacted binder composition, and the pre-reacted binder composition comprising the reaction product(s) of (a) at least one carbohydrate component selected from the group consisting of dextrose, glucose, fructose and mixtures thereof, and (b) hexamethylenediamine, wherein the pre-reacted binder composition comprises at least one pre-polymer having a molecular weight in the range of 1 to 500 kDa in an amount of 2 wt.-% or more, based on the total weight of the pre-reacted binder composition; (iii) applying the aqueous solution or dispersion to the collection of matter; and (iv) applying energy to the collection of matter containing said aqueous solution or dispersion to cure the binder composition.

2. The method of claim 1, wherein providing a water-soluble pre-reacted binder composition in the form of an aqueous solution or dispersion comprises reacting (a) the at least one carbohydrate component and (b) hexamethylenediamine at temperature(s) of at least 30° C. during period(s) of at least 5 minutes.

3. The method of claim 1, wherein said method has at least one of the following features: said at least one pre-polymer having a molecular weight in the range of 1 to 500 kDa is contained in the pre-reacted binder composition in an amount of 5 wt.-% or more based on the total weight of the binder composition; said at least one pre-polymer having a molecular weight in the range of 1 to 500 kDa is contained in the pre-reacted binder composition in an amount of 10 wt.-% or more based on the total weight of the binder composition; said at least one pre-polymer having a molecular weight in the range of 1 to 500 kDa is contained in the pre-reacted binder composition in an amount of 20 wt.-% or more based on the total weight of the binder composition; said at least one pre-polymer having a molecular weight in the range of 1 to 500 kDa is contained in the pre-reacted binder composition in an amount of 35 wt.-% or more based on the total weight of the binder composition; said at least one pre-polymer having a molecular weight in the range of 1 to 500 kDa is contained in the pre-reacted binder composition in an amount of 50 wt.-% or more based on the total weight of the binder composition.

4. The method of claim 1, wherein said method has at least one of the following features: said pre-reacted binder composition comprises at least one pre-polymer having a molecular weight in the range of more than 80 to 500 kDa (high molecular-weight pre-polymer); said pre-reacted binder composition comprises at least one pre-polymer having a molecular weight in the range of more than 80 to 500 kDa in an amount of 0.2 wt.-% or more, based on the total weight of the pre-reacted binder composition; said pre-reacted binder composition comprises at least one pre-polymer having a molecular weight in the range of more than 80 to 500 kDa in an amount of 0.5 wt.-% or more, based on the total weight of the pre-reacted binder composition; said pre-reacted binder composition comprises at least one pre-polymer having a molecular weight in the range of more than 80 to 500 kDa in an amount of 0.75 wt.-% or more, based on the total weight of the pre-reacted binder composition.

5. The method of claim 1, wherein said method has at least one of the following features: said pre-reacted binder composition comprises at least one pre-polymer having a molecular weight in the range of more than 10 to 80 kDa (mid molecular weight pre-polymer); said pre-reacted binder composition comprises at least one pre-polymer having a molecular weight in the range of more than 10 to 80 kDa in an amount of 0.3 wt.-% or more, based on the total weight of the pre-reacted binder composition; said pre-reacted binder composition comprises at least one pre-polymer having a molecular weight in the range of more than 10 to 80 kDa in an amount of 1 wt.-% or more, based on the total weight of the pre-reacted binder composition; said pre-reacted binder composition comprises at least one pre-polymer having a molecular weight in the range of more than 10 to 80 kDa in an amount of 5 wt.-% or more, based on the total weight of the pre-reacted binder composition; said pre-reacted binder composition comprises at least one pre-polymer having a molecular weight in the range of more than 10 to 80 kDa in an amount of 10 wt.-% or more, based on the total weight of the pre-reacted binder composition; said pre-reacted binder composition comprises at least one pre-polymer having a molecular weight in the range of more than 10 to 80 kDa in an amount of 30 wt.-% or more, based on the total weight of the pre-reacted binder composition; said pre-reacted binder composition comprises at least one pre-polymer having a molecular weight in the range of more than 10 to 80 kDa in an amount of 50 wt.-% or more, based on the total weight of the pre-reacted binder composition.

6. The method of claim 1, wherein said method has at least one of the following features: said pre-reacted binder composition comprises one or more compounds having a molecular weight of 10 kDa or less (low molecular-weight compounds), and which are different from (a) the at least one carbohydrate component and (b) hexamethylenediamine; said pre-reacted binder composition comprises one or more compounds having a molecular weight of 10 kDa or less (low molecular-weight compounds), and which are different from (a) the at least one carbohydrate component and (b) hexamethylenediamine, in which the low molecular-weight compounds comprise one or more of a glycolaldehyde, glyceraldehyde, 2-oxopropanal, acetol, dihydroxyacetone, acetoin, butanedione, ethanal, glucosone, 1-desoxyhexosulose, 3-desoxyhexosulose, 3-desoxy-pentosulose, 1,4-didesoxyhexosulose, glyoxal, methylglyoxal, diacetyl and 5-(hydroxymethyl)furfural.

7. The method of claim 1, wherein said method has at least one of the following features: said aqueous solution or dispersion contains at least 30 wt.-% of said pre-reacted binder composition; said aqueous solution or dispersion contains at least 40 wt.-% of said pre-reacted binder composition; said aqueous solution or dispersion contains at least 50 wt.-% of said pre-reacted binder composition; said aqueous solution or dispersion contains at least 55 wt.-% of said pre-reacted binder composition.

8. The method of claim 1, wherein when the water-soluble pre-reacted binder composition in the form of an aqueous solution or dispersion contains 70 wt.-% of said pre-reacted binder composition, the viscosity at 20° C. is at most 2000 cP.

9. The method of claim 1, in which the viscosity of an aqueous solution containing 70 wt.-% of said pre-reacted binder composition does not increase by more than 500 cP when left to stand at 20° C. for 12 hours.

10. The method of claim 1, further comprising storing and subsequently adding a crosslinker to said pre-reacted binder composition prior to curing the binder composition.

11. The method of claim 10, wherein the crosslinker comprises hexamethylenediamine.

12. The method of claim 1, wherein the ratio of total carbonyl groups in the carbohydrate component(s) to total reactive nitrogen-containing groups in the hexamethylenediamine from which the reaction products of the pre-reacted binder composition formed is 5:1 to 1:5.

13. The method of claim 1, wherein the weight ratio between the carbohydrate component and the hexamethylenediamine from which the reaction products of the prereacted binder composition is formed is 0.5:1 to 30:1.

14. The method of claim 1, wherein the pre-reacted binder composition has a bake-out solid content of at least 5 wt. % and no more than 60 wt. %, determined as bake out solids by weight after drying at 140° C. for 2 hours.

15. The method of claim 1, wherein the reaction products are formed by reaction of (a) the at least one carbohydrate component and (b) hexamethylenediamine at temperature(s) of at most 120° C.

16. The method of claim 1, wherein the reaction products are formed by reaction of (a) the at least one carbohydrate component and (b) hexamethylenediamine during period(s) of at most 96 hours.

17. The method of claim 1, wherein the reaction products are formed by a reaction of (a) the at least one carbohydrate component and (b) hexamethylenediamine at a temperature range of 40 to 120° C. for a period of 5 to 180 minutes.

18. The method of claim 1, wherein the reaction products are formed by reaction of (a) the at least one carbohydrate component and (b) hexamethylenediamine at a temperature range of 20 to 30° C. for a period of 1 to 96 hours.

19. The method of claim 1, wherein the pre-reacted binder composition has been aged for at least 24 hours before applying energy to the collection of matter.

20. The method of claim 1, wherein prior to applying the solution or dispersion to the collection of matter, the collection of matter is substantially free of binder.

21. The method of claim 1, wherein said pre-reacted binder composition comprises at least one pre-polymer having a molecular weight in the range of more than 80 to 500 kDa and at least one pre-polymer having a molecular weight in the range of more than 10 to 80 kDa.

22. The method of claim 1, wherein said pre-reacted binder composition comprises at least one pre-polymer having a molecular weight in the range of more than 80 to 500 kDa in an amount of 0.2 wt.-% or more, and at least one pre-polymer having a molecular weight in the range of more than 10 to 80 kDa in an amount of 0.3 wt.-% or more.

23. The method of claim 1, wherein said pre-reacted binder composition comprises at least one pre-polymer having a molecular weight in the range of more than 80 to 500 kDa, at least one pre-polymer having a molecular weight in the range of more than 10 to 80 kDa, and one or more compounds having a molecular weight of 10 kDa or less which are different from (a) the at least one carbohydrate component and (b) hexamethylenediamine.

24. The method of claim 1, wherein said pre-reacted binder composition comprises at least one pre-polymer having a molecular weight in the range of more than 80 to 500 kDa in an amount of 0.2 wt.-% or more; at least one pre-polymer having a molecular weight in the range of more than 10 to 80 kDa in an amount of 0.3 wt.-% or more, and one or more compounds having a molecular weight of 10 kDa or less which are different from (a) the at least one carbohydrate component and (b) hexamethylenediamine.

* * * * *